US009956078B2

(12) United States Patent
Yaron

(10) Patent No.: US 9,956,078 B2
(45) Date of Patent: May 1, 2018

(54) HEART VALVE REPAIR DEVICES AND METHODS

(71) Applicant: MITRALIX LTD., Rehovot (IL)

(72) Inventor: Ira Yaron, Har Adar (IL)

(73) Assignee: MITRALIX LTD., Rehovot (IL)

( * ) Notice: Subject to any disclaimer, the term of this patent is extended or adjusted under 35 U.S.C. 154(b) by 0 days. days.

(21) Appl. No.: 15/153,526

(22) Filed: May 12, 2016

(65) Prior Publication Data

US 2016/0256276 A1    Sep. 8, 2016

Related U.S. Application Data

(63) Continuation of application No. 13/529,451, filed on Jun. 21, 2012, now Pat. No. 9,364,326.

(60) Provisional application No. 61/550,513, filed on Oct. 24, 2011, provisional application No. 61/502,573, filed on Jun. 29, 2011.

(51) Int. Cl.
*A61F 2/24* (2006.01)

(52) U.S. Cl.
CPC .......... *A61F 2/2457* (2013.01); *A61F 2/2427* (2013.01); *A61F 2/2445* (2013.01); *A61F 2/2409* (2013.01); *A61F 2210/0004* (2013.01); *A61F 2210/0014* (2013.01); *A61F 2220/0016* (2013.01); *A61F 2230/0091* (2013.01); *A61F 2250/001* (2013.01); *A61F 2250/006* (2013.01); *A61F 2310/00011* (2013.01)

(58) Field of Classification Search
CPC .......................................... A61F 2/24
USPC ................. 623/2.1, 2.11, 2.34–2.38
See application file for complete search history.

(56) References Cited

U.S. PATENT DOCUMENTS

| 2,108,206 A | 2/1938 | Meeker |
| 3,378,010 A | 4/1968 | Codling et al. |
| 4,602,911 A | 7/1986 | Ahmadi et al. |
| 4,972,874 A | 11/1990 | Jackson |
| 5,350,397 A | 9/1994 | Palermo et al. |
| 5,593,424 A | 1/1997 | Northrup, III |

(Continued)

FOREIGN PATENT DOCUMENTS

| EP | 2 072 021 A1 | 6/2009 |
| JP | 2009-502324 A | 1/2009 |

(Continued)

OTHER PUBLICATIONS

International Search Report and Written Opinion of the International Searching Authority in International Application No. PCT/IB2015/001026, dated Oct. 23, 2015.

(Continued)

*Primary Examiner* — Yashita Sharma
(74) *Attorney, Agent, or Firm* — Kacvinsky Daisak Bluni PLLC; Douglas E. Ringel

(57) ABSTRACT

Devices and methods for the repair of the functioning of heart valves are provided. A device may comprise a first section having a generally spiral shape and a second section connected to the first section. A method involves positioning the device such that chords associated with the heart valve are positioned within the path of the generally spiral shape of the first section and positioning the second section on an opposite side of the heart valve. The first section may be turned in a manner such that the chords move closer to the center of the first section. The first section draws the chords closer together, thereby pulling the valve leaflets closer together in order to facilitate their coaptation and proper closing.

34 Claims, 12 Drawing Sheets

(56) References Cited

U.S. PATENT DOCUMENTS

| | | |
|---|---|---|
| 5,810,882 A | 9/1998 | Bolduc et al. |
| 6,183,512 B1 | 2/2001 | Howanec, Jr. et al. |
| 6,217,610 B1 | 4/2001 | Carpentier et al. |
| 6,332,893 B1 | 12/2001 | Mortier et al. |
| 6,348,068 B1 | 2/2002 | Campbell et al. |
| 6,371,464 B1 | 4/2002 | Porche et al. |
| 6,425,916 B1 | 7/2002 | Garrison et al. |
| 6,454,799 B1 | 9/2002 | Schreck |
| 6,461,366 B1 | 10/2002 | Seguin |
| 6,544,272 B1 | 4/2003 | Jakob et al. |
| 6,629,534 B1 | 10/2003 | St. Goar et al. |
| 6,730,118 B2 | 5/2004 | Spenser et al. |
| 6,752,813 B2 | 6/2004 | Goldfarb et al. |
| 6,770,083 B2 | 8/2004 | Seguin |
| 6,786,924 B2 | 9/2004 | Ryan et al. |
| 6,797,002 B2 | 9/2004 | Spence et al. |
| 6,893,460 B2 | 5/2005 | Spenser et al. |
| 7,048,754 B2 | 5/2006 | Martin et al. |
| 7,077,861 B2 | 7/2006 | Spence |
| 7,166,127 B2 | 1/2007 | Spence et al. |
| 7,189,199 B2 | 3/2007 | McCarthy et al. |
| 7,226,467 B2 | 6/2007 | Lucatero et al. |
| 7,288,097 B2 | 10/2007 | Séguin |
| 7,316,706 B2 | 1/2008 | Bloom et al. |
| 7,544,206 B2 | 6/2009 | Cohn |
| 7,563,267 B2 | 7/2009 | Goldfarb et al. |
| 7,563,273 B2 | 7/2009 | Goldfarb et al. |
| 7,604,646 B2 | 10/2009 | Goldfarb et al. |
| 7,608,091 B2 | 10/2009 | Goldfarb et al. |
| 7,635,329 B2 | 12/2009 | Goldfarb et al. |
| 7,655,015 B2 | 2/2010 | Goldfarb et al. |
| 7,666,204 B2 | 2/2010 | Thornton et al. |
| 7,682,319 B2 | 3/2010 | Martin et al. |
| 7,682,369 B2 | 3/2010 | Séguin |
| 7,691,143 B2 | 4/2010 | Wright et al. |
| 7,699,892 B2 | 4/2010 | Rafiee et al. |
| 7,704,269 B2 | 4/2010 | St Goar et al. |
| 7,736,388 B2 | 6/2010 | Goldfarb et al. |
| 7,763,923 B2 | 7/2010 | St. Goar et al. |
| 7,803,187 B2 | 9/2010 | Hauser |
| 7,811,296 B2 | 10/2010 | Goldfarb et al. |
| 7,896,915 B2 | 3/2011 | Guyenot et al. |
| 7,951,195 B2 | 5/2011 | Antonsson et al. |
| 7,967,857 B2 | 6/2011 | Lane |
| 8,128,691 B2 | 3/2012 | Keränen |
| 8,968,393 B2 | 3/2015 | Rothstein |
| 8,998,933 B2 | 4/2015 | Rothstein et al. |
| 2001/0034551 A1 | 10/2001 | Cox |
| 2001/0041933 A1 | 11/2001 | Thoma |
| 2002/0013571 A1 | 1/2002 | Goldfarb et al. |
| 2002/0035361 A1 | 3/2002 | Houser et al. |
| 2002/0151970 A1 | 10/2002 | Garrison et al. |
| 2002/0183766 A1 | 12/2002 | Seguin |
| 2003/0149476 A1 | 8/2003 | Damm et al. |
| 2003/0167071 A1 | 9/2003 | Martin et al. |
| 2004/0003819 A1 | 1/2004 | St. Goar et al. |
| 2004/0030382 A1 | 2/2004 | St Goar et al. |
| 2004/0039442 A1 | 2/2004 | St Goar et al. |
| 2004/0044350 A1 | 3/2004 | Martin et al. |
| 2004/0049207 A1 | 3/2004 | Goldfarb et al. |
| 2004/0087975 A1 | 5/2004 | Lucatero et al. |
| 2004/0092962 A1 | 5/2004 | Thornton et al. |
| 2004/0162610 A1 | 8/2004 | Liska et al. |
| 2004/0225300 A1 | 11/2004 | Goldfarb et al. |
| 2004/0236354 A1 | 11/2004 | Seguin |
| 2004/0267357 A1 | 12/2004 | Allen et al. |
| 2005/0021056 A1 | 1/2005 | St. Goar et al. |
| 2005/0021057 A1 | 1/2005 | St Goar et al. |
| 2005/0033446 A1 | 2/2005 | Deem et al. |
| 2005/0075659 A1 | 4/2005 | Realyvasquez et al. |
| 2005/0143811 A1 | 6/2005 | Realyvasquez |
| 2005/0140014 A1 | 7/2005 | Hauck et al. |
| 2005/0240202 A1 | 10/2005 | Shennib et al. |
| 2006/0020275 A1 | 1/2006 | Goldfarb et al. |
| 2006/0089671 A1 | 4/2006 | Goldfarb et al. |
| 2006/0135993 A1 | 6/2006 | Seguin |
| 2006/0184203 A1 | 8/2006 | Martin et al. |
| 2006/0195134 A1 | 8/2006 | Crittenden |
| 2006/0276871 A1 | 12/2006 | Lamson et al. |
| 2006/0282161 A1 | 12/2006 | Huynh et al. |
| 2007/0078297 A1 | 4/2007 | Rafiee et al. |
| 2007/0100356 A1 | 5/2007 | Lucatero et al. |
| 2007/0100439 A1 | 5/2007 | Cangialosi |
| 2007/0112421 A1 | 5/2007 | O'Brien |
| 2007/0118155 A1 | 5/2007 | Goldfarb et al. |
| 2007/0129737 A1 | 6/2007 | Goldfarb et al. |
| 2007/0197858 A1 | 8/2007 | Goldfarb et al. |
| 2007/0255396 A1 | 11/2007 | Douk et al. |
| 2008/0051703 A1 | 2/2008 | Thornton et al. |
| 2008/0051807 A1 | 2/2008 | St. Goar et al. |
| 2008/0071365 A1 | 3/2008 | Ley |
| 2008/0097489 A1 | 4/2008 | Goldfarb et al. |
| 2008/0167702 A1 | 7/2008 | Ransbury et al. |
| 2008/0167714 A1 | 7/2008 | St. Goar et al. |
| 2008/0183194 A1 | 7/2008 | Goldfarb et al. |
| 2008/0208330 A1 | 8/2008 | Keränen |
| 2008/0228272 A1 | 9/2008 | Moaddeb et al. |
| 2009/0105815 A1 | 4/2009 | Krever et al. |
| 2009/0156995 A1 | 6/2009 | Martin et al. |
| 2009/0163934 A1 | 6/2009 | Raschdorf, Jr. et al. |
| 2009/0198322 A1 | 8/2009 | Deem et al. |
| 2009/0198324 A1 | 8/2009 | Orlov |
| 2009/0222026 A1 | 9/2009 | Rothstein et al. |
| 2009/0259210 A1 | 10/2009 | Sabbah |
| 2009/0270858 A1 | 10/2009 | Hauck et al. |
| 2009/0326567 A1 | 12/2009 | Goldfarb et al. |
| 2010/0010538 A1 | 1/2010 | Juravic et al. |
| 2010/0016958 A1 | 1/2010 | St. Goar et al. |
| 2010/0022823 A1 | 1/2010 | Goldfarb et al. |
| 2010/0023118 A1 | 1/2010 | Medlock et al. |
| 2010/0094317 A1 | 4/2010 | Goldfarb et al. |
| 2010/0100108 A1 | 4/2010 | Goldfarb et al. |
| 2010/0130924 A1 | 5/2010 | Martin et al. |
| 2010/0179648 A1 | 7/2010 | Richter et al. |
| 2010/0179649 A1 | 7/2010 | Richter et al. |
| 2010/0185275 A1 | 7/2010 | Richter et al. |
| 2010/0191256 A1 | 7/2010 | Séguin |
| 2010/0204662 A1 | 8/2010 | Orlov et al. |
| 2010/0210899 A1 | 8/2010 | Schankereli |
| 2010/0217283 A1 | 8/2010 | St Goar et al. |
| 2010/0262167 A1 | 10/2010 | Jelich et al. |
| 2010/0280603 A1 | 11/2010 | Maisano et al. |
| 2010/0298929 A1 | 11/2010 | Thornton et al. |
| 2010/0298930 A1 | 11/2010 | Orlov |
| 2010/0331971 A1 | 12/2010 | Keranen et al. |
| 2011/0004227 A1 | 1/2011 | Goldfarb et al. |
| 2011/0029055 A1 | 2/2011 | Tidemand |
| 2011/0054306 A1 | 3/2011 | del Nido et al. |
| 2011/0071626 A1 | 3/2011 | Wright et al. |
| 2011/0077733 A1 | 3/2011 | Solem |
| 2014/0194975 A1 | 7/2014 | Quill et al. |
| 2015/0032204 A1 | 1/2015 | Johansson |

FOREIGN PATENT DOCUMENTS

| | | |
|---|---|---|
| WO | 2000/047139 A1 | 8/2000 |
| WO | 2000/060995 A2 | 10/2000 |
| WO | 2003/020179 A1 | 3/2003 |
| WO | 2004/112651 A2 | 12/2004 |
| WO | 2005/087139 A1 | 9/2005 |
| WO | 2006/091163 A1 | 6/2006 |
| WO | 2007/015876 A1 | 2/2007 |
| WO | 2007/030063 A1 | 3/2007 |
| WO | 2011/057087 A1 | 5/2011 |
| WO | 2012/094406 A1 | 7/2012 |
| WO | 2012/095116 A1 | 7/2012 |

OTHER PUBLICATIONS

Paul T. L. Chiam, MBBS, et al., "Percutaneous Transcatheter Mitral Valve Repare, A Classification of the Technology," JACC: Cardiovascular Interventions, vol. 4, No. 1, 2011, pp. 1-13, published by Elsevier Inc., Jan. 2011.

(56) References Cited

OTHER PUBLICATIONS

Mitral Valve Information from <http://mitralvalverepair.org/>, Mount Sinai Medical Center, Department of Cardiothoracic Surgery, New York, NY (last updated Jan. 2011).
Gregg W. Stone, MD, "Overview of Percutaneous Mitral Valve Therapies," Columbia University Medical Center, The Cardiovascular Research Foundation (31 pages) (2009).
European Patent Office, International Search Report and Written Opinion in International Application No. PCT/IB12/01253, dated Jan. 7, 2013.

HEART VALVE REPAIR DEVICES AND METHODS

CROSS REFERENCE TO RELATED APPLICATIONS

The present application is a continuation of and claims priority to pending U.S. patent application Ser. No. 13/529,451 filed. Jun. 21, 2012, which claims priority to U.S. provisional application Ser. No. 61/502,573 filed Jun. 29, 2011, and to U.S. provisional application Ser. No. 61/550,513 filed Oct. 24, 2011, the disclosures of which are incorporated herein by reference in their entirety.

FIELD OF THE INVENTION

The invention relates to devices and methods for the repair of the functioning of heart valves, in particular the mitral valve.

BACKGROUND OF THE INVENTION

Heart valves regulate the movement of blood into and out of the chambers of the heart. The mitral valve, positioned between the left atrium and the left ventricle, can be subject to a condition known as mitral regurgitation, in which the mitral valve does not close properly and some backflow of blood occurs from the left ventricle back into the left atrium. For example, a mitral valve leaflet can experience prolapse during systole, thereby inhibiting leaflet coaptation and permitting backflow of blood into the left atrium.

Various procedures and devices have been proposed to address the condition of mitral regurgitation. For example, some mitral valve repair procedures involve removing a section of a valve leaflet in order to reduce its propensity for prolapse. Other procedures involve mitral valve replacement. The MITRACLIP (Abbott Vascular) is a device intended to be positioned across the mitral valve to create a double orifice, in an effort to allow the valve to close fully during systole.

Despite these efforts, there is a continuing need for improved treatment for mitral valve regurgitation and for the repair of the functioning of heart valves in general. The various procedures and devices previously proposed can be improved upon in terms of their overall clinical outcome, ease of use, reduction of procedure time and risk, and/or reduction of cost.

SUMMARY OF THE INVENTION

The present invention provides devices and methods for the repair of the functioning of heart valves.

In some embodiments, the device comprises a first section having a generally spiral shape adapted to be positioned on a ventricular side of the heart valve such that chords associated with the heart valve are positioned within the path of the generally spiral shape of the first section and a second section adapted to be positioned on an atrial side of the heart valve, wherein the first section is connected to the second section. The first section is designed to draw chords associated with the heart valve closer together, thereby pulling the valve leaflets closer together in order to facilitate their coaptation and proper closing. The second section aids in keeping the first section in position. The second section can also aid in maintaining or reducing the size of the annulus.

In some embodiments of a method of repairing a heart valve, a heart valve assisting device is delivered to the area of the heart valve, wherein the device comprises a first section having a generally spiral shape and a second section connected to the first section. The method further includes positioning the first section on a ventricular side of the heart valve such that chords associated with the heart valve are positioned within the path of the generally spiral shape of the first section and positioning the second section on an atrial side of the heart valve. The step of positioning the first section may further include turning the first section in a first direction such that the chords move closer to the center of the first section. This movement of the chords pulls the valve leaflets closer together in order to facilitate their coaptation and proper closing. The second section aids in keeping the first section in position. The second section can also aid in maintaining or reducing the size of the annulus.

DETAILED DESCRIPTION

Certain embodiments of heart valve repair devices and methods of using them are described herein with reference to the accompanying drawings. These embodiments are only examples, as numerous variations of the invention disclosed herein are possible within the scope of the appended claims.

Figure 1:
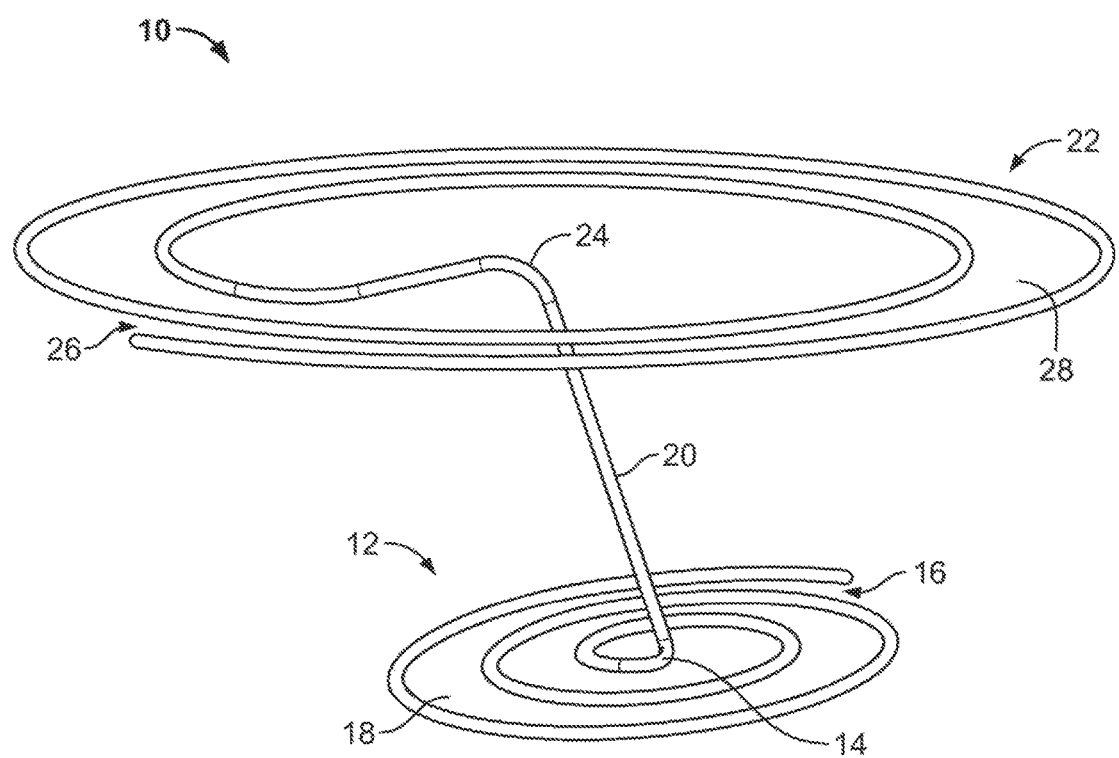
FIG. 1 shows a perspective view of a first embodiment of a heart valve assisting device.

FIG. 1 shows a first embodiment of a heart valve assisting device 10. The device 10 comprises a first or lower section 12, a second or upper section 22, and a connector 20. As described below, the first or lower section can function as a coaptation section, and the second or upper section can function as a stabilizing or anchoring section.

The term "spiral" is used herein to refer broadly to shapes defined by a structure forming a winding around a center wherein the winding gradually moves away from the center as it winds around the center. The winding may move away from the center at a constant rate or at a non-constant rate, and the general outline of the spiral may take various shapes, such as substantially circular, substantially elliptical, or other shapes. The spiral may be symmetrical or asymmetrical, and the center around which the winding structure winds may be a point at the geometric center of the spiral or a point that is offset from the geometric center of the spiral. The winding may be in one plane, such that the spiral is substantially flat. Alternatively, the winding may not be in one plane, with the winding moving up or down at a constant or non-constant rate. Thus, for example, the spiral may be substantially conical. The winding may make multiple turns around the center or less than a full turn around the center. The winding structure of the spiral forms a path that starts from an opening at the outer periphery of the spiral and that moves toward the center of the spiral as the path winds around the center of the spiral.

As can be seen in FIG. 1, the first section 12 has a generally spiral shape. The spiral shape is defined by the wire structure of the first section 12 forming a winding around a center 14 of the first section, wherein the winding gradually moves away from the center 14 as it winds around the center 14. In the case of FIG. 1, the winding of the first section 12 moves away from the center 14 at a generally constant rate, and the general outline of the spiral of first section 12 has a substantially circular shape, which can be seen in the top view of FIG. 2.

Figure 3:
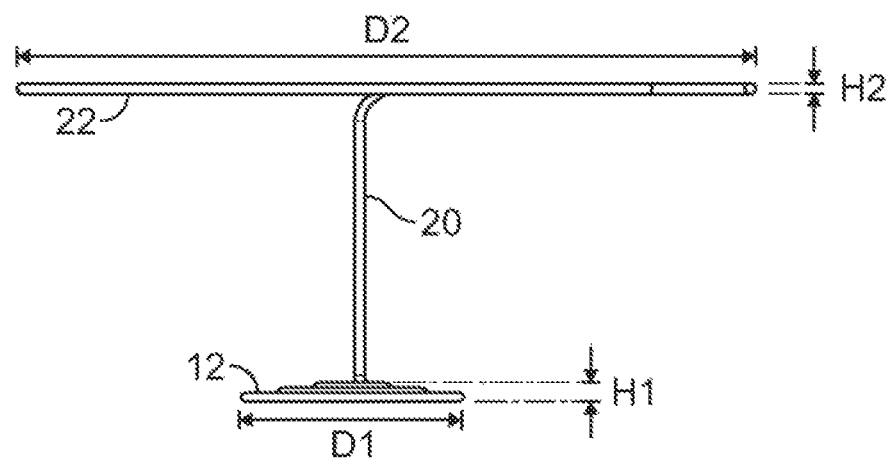
FIG. 3 shows a side view of the heart valve assisting device of FIG. 1.

As can be seen in the side view of FIG. 3, the winding of the first section 12 moves gradually out of plane. Thus, the winding of the first section 12 has a height H1 that is greater than the thickness of the wire structure forming the first section 12.

Figure 2:
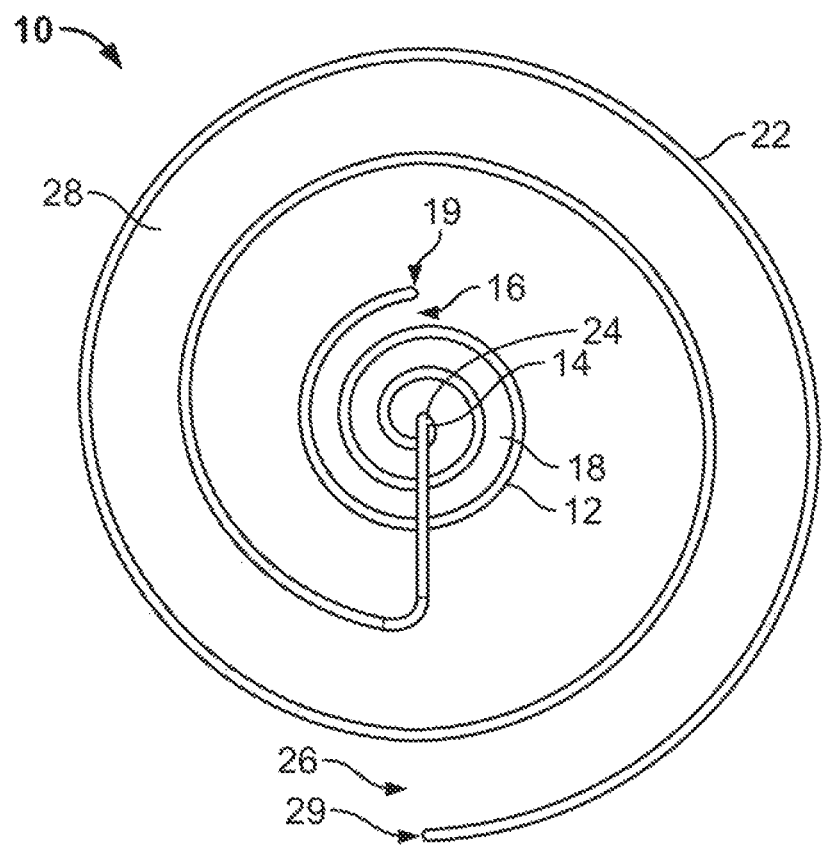
FIG. 2 shows a top view of the heart valve assisting device of FIG. 1.

As shown in FIGS. 1 and 2, the winding structure of the first section 12 forms a path 18 that starts from an opening 16 at the outer periphery of the spiral and that moves toward the center 14 of the spiral as the path 18 winds around the center 14 of the spiral. In this illustrated embodiment, the path comprises about two and one-half turns around the center 14. More or fewer turns may be used.

As described above, the spiral may take other shapes. In addition the first section may be comprised of more than one spiral. For example, the first section may have two, three, four or more spirals, which may be similar or dissimilar to each other. In one example, two spirals may emanate from a common center, each being similar to the other except starting in a direction that is 180 degrees from the other. This example results in nested spirals in which the opening of each of the spirals is 180 degrees from the opening of the other spiral. In other examples, three spirals may emanate from a common center, starting 120 degrees apart and having openings 120 degrees apart, or four spirals may emanate from a common center, starting 90 degrees apart and having openings 90 degrees apart.

In the embodiment of FIGS. 1-3, the second section 22 also has a generally spiral shape. As with the first section 12, in the case of FIG. 1, the winding of the second section 22 moves away from the center 24 of the second section 22 at a generally constant rate, and the general outline of the spiral of second section 22 has a substantially circular shape, which can be seen in the top view of FIG. 2. The overall diameter D2 of the second section 22 is larger than the overall diameter D1 of the first section 12. In one example, the overall diameter D2 of the second section may be approximately 2.0-5.0 centimeters (e.g., 4.0 centimeters), and the overall diameter D1 of the first section may be approximately 1.0-2.0 centimeters (e.g., 1.2 centimeters), but larger or smaller diameters are possible for both the first section and the second section.

As can be seen in the side view of FIG. 3, the winding of the second section 22 generally stays in one plane. Thus, the winding of the second section 22 has a height H2 that is substantially the same as the thickness of the wire structure forming the second section 22.

As shown in FIGS. 1 and 2, the winding structure of the second section 22 forms a path 28 that starts from an opening 26 at the outer periphery of the spiral and that moves toward the center 24 of the spiral as the path 28 winds around the center 24 of the spiral. In this illustrated embodiment, the path comprises about two turns around the center 24. More or fewer turns may be used. As described above, the spiral of the second section may take other shapes, and the second section may be comprised of more than one spiral.

The first section 12 is connected to the second section 22 by a connector 20. The connector 20, as can be seen in FIGS. 1 and 3, is substantially straight. In alternative embodiments, the connector connecting the first section and the second section may be curved, bent, helical, or any other suitable shape. In one example, the length of the connector may be approximately 1.0-2.0 centimeters (e.g., 1.5 centimeters), but longer or shorter lengths are possible.

The device 10, including the first section 12, the second section 22 and the connector 20, is comprised of a wire. In alternative embodiments, all or part of the device comprises a wire, bundle of wires, strip, rod or tube, and different sections of the device or parts thereof may comprise a wire, bundle of wires, strip, rod, tube or a combination thereof. The structure may be formed by bending or otherwise shaping a wire, bundle of wires, strip, rod or tube into the desired shape. Alternatively, the shape may be formed as the wire, bundle of wires, strip, rod, or tube is formed. For example, the spiral shape of the first section may be chemically or laser etched or otherwise cut from a sheet of material, in which case the strip or rod is formed simultaneously with the spiral shape. The device may be formed of more than a single structure or material; for example, a tube with wire core may form the upper section, the lower section and/or the connector between them, with the other element(s) formed of a similar or dissimilar structural component.

The use of a bundle of wires can provide the device with high axial strength as well as high flexibility. For example, the use of several thin wires in a twisted bundle or in a braided bundle provides high axial strength and flexibility that can be determined by the twisting or braiding structure.

The wire, bundle of wires, strip, rod or tube may have any suitable cross-sectional shape. For example, the wire, bundle of wires, strip, rod or tube may have a circular, elliptical, square, rectangular, hexagonal or other cross-sectional shape. The wire, bundle of wires, strip, rod or tube may have different cross-sectional shapes or sizes at different places along its length. The wire of device 10 has a circular cross-sectional shape along its length. In one example, the wire, bundle of wires, strip, rod or tube may have a diameter, width or thickness of approximately 0.2-1.0 millimeters (e.g., 0.4 millimeters), but larger or smaller dimensions are possible.

The wire of device 10 is formed from a suitable shape memory metal, for example nitinol. Other suitable materials may be used for all or part of the wire(s), rod(s) or tube(s) of the device, for example other shape memory materials, other metallic materials, plastic materials and/or composite materials.

The device 10 of FIGS. 1-3 has ends 19, 29 at the ends of the wire forming the device. These ends may be rounded. In alternative embodiments, one or more ends of the wire, bundle of wires, strip, rod or tube may be rounded, squared-off, pointed, or may have an anchoring element positioned on it, for example on the end of the second section for holding the device in position. As described further below, the second section may have one or more anchoring elements for anchoring the device to heart tissue. For example, barbs or hooks may be formed on the second section 22, and/or the second section 22 may be provided with one or more loops to facilitate suturing the second section 22 in place. Such anchoring elements may be placed at the end of the spiral, along the outer wind of the spiral, and/or at any other suitable position.

As can be seen in the top view of FIG. 2, the spiral of first section 12 can be considered as being wound in a clockwise direction when viewed from the top and starting from the center and moving outward. Similarly, the spiral of second section 22 also can be considered as being wound in a clockwise direction when viewed from the top and starting from the center and moving outward. Thus, both first section 12 and second section 22 have windings in the same direction. In an alternative embodiment, the spiral of the second section 22 can be wound in an opposite direction from that of the spiral of the first section 12.

The wire, bundle of wires, strip, rod or tube may have one or more grooves in its outer surface. The groove in the outer surface of the wire, bundle of wires, strip, rod or tube may extend around the perimeter of the wire, bundle of wires, strip, rod or tube and/or in the direction of the length of the wire, bundle of wires, strip, rod or tube. As one example, the wire, bundle of wires, strip, rod or tube may have one more grooves that extend in a substantially helical path along the wire, bundle of wires, strip, rod or tube. Such grooves may serve different purposes. For example, one or more grooves may be used to create different flexibilities at different places of the device, to facilitate ingrowth of tissue, to facilitate grasping and manipulation (e.g., pushing, pulling, turning, etc.) of the device, and/or as channels for drug delivery. For example, a helical groove can be used to facilitate rotation of the device as it is being delivered from or withdrawn into a delivery catheter. Similarly, a helical or other groove can direct cell growth in layers in a preferred direction, thereby reducing scar formation.

The wire, bundle of wires, strip, rod or tube may have one or more holes in it. The holes may be through-holes extending all the way through the thickness of the wire, bundle of wires, strip, rod or tube, and/or the holes may be pockets or dimples in the outer surface of the wire, bundle of wires, strip, rod or tube. The holes may be a series of holes extending along the length and around the periphery of the wire, bundle of wires, strip, rod or tube. The holes may serve different purposes. For example, one or more holes may be used to create different flexibilities at different places of the device, to facilitate ingrowth of tissue, to facilitate grasping and manipulation of the device, to provide ports for injection of a contrast agent, and/or as sites for drug delivery.

The device may comprise a coating on the wire, bundle of wires, strip, rod or tube. The coating is preferably a biocompatible coating that may be used, for example, to reduce possible negative reactions from the tissue where the device is implanted, to reduce friction (as a lubricious coating) to assist in delivery of the device, to reduce friction in areas where the device is designed to be moved against tissue (for example, along the path of the spiral of the first section), to increase friction in areas where it is desired to reduce movement or to anchor the device (for example, in the second section), to deliver a suitable drug, for radiopacity, to encourage cell and tissue growth that would assist in fixation (e.g., of the upper section), to encourage tissue growth between the chords and/or leaflets, and/or for other purposes. With respect to radiopacity, the entire device or selected points on the device may be coated or plated with a material allowing the physician to understand the location of the device during and/or after the implantation procedure. For example, the ends of the spirals and/or the connector may be plated with a radiopaque material. If selected points on the device are plated, the plating at the selected points may have a certain shape (e.g., a line, arrow, etc.) to assist in understanding the orientation of the device. In another example, in the case of a device formed of a tube, the tube may be coated to ensure that the coated tube is sealed in order that the tube may be used, for example, for pressure measurement. When the coating is a drug-release coating, the coating may comprise a carrier (for example, a polymer) with the drug in the carrier for drug elution over a suitable period of time. The drug eluting mechanism may use a biodegradable carrier (e.g., a biodegradable polymer) or a stable carrier (e.g., a stable polymer) that allows the drug elution through diffusion of drug molecules.

Figure 4:
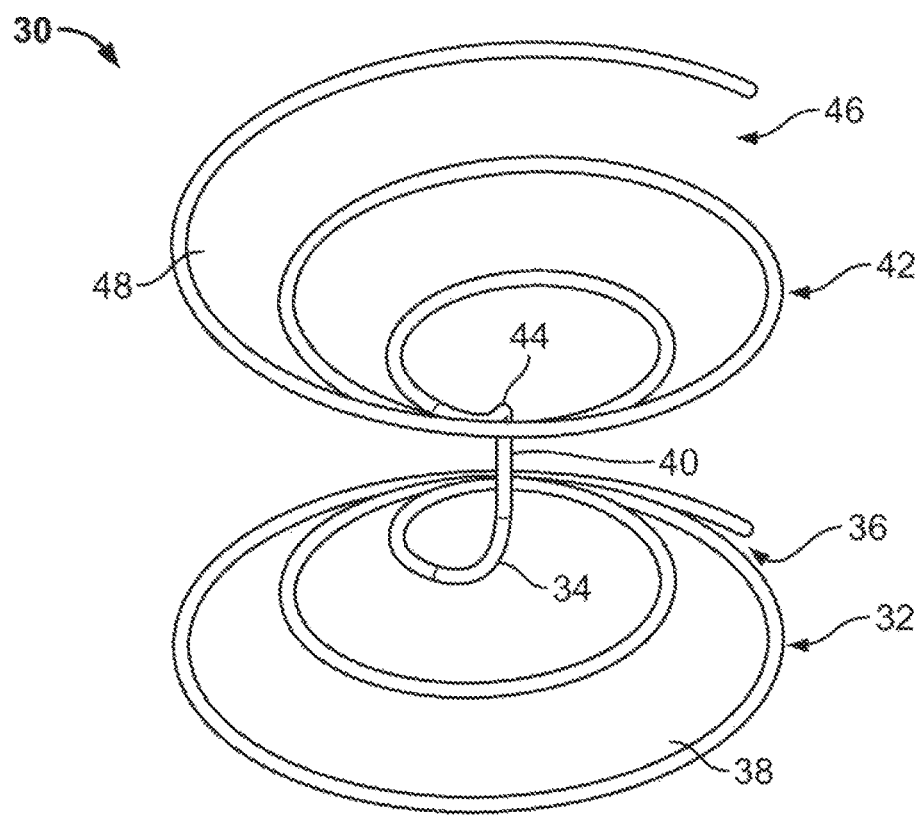
FIG. 4 shows a perspective view of a second embodiment of a heart valve assisting device.
Figure 5:
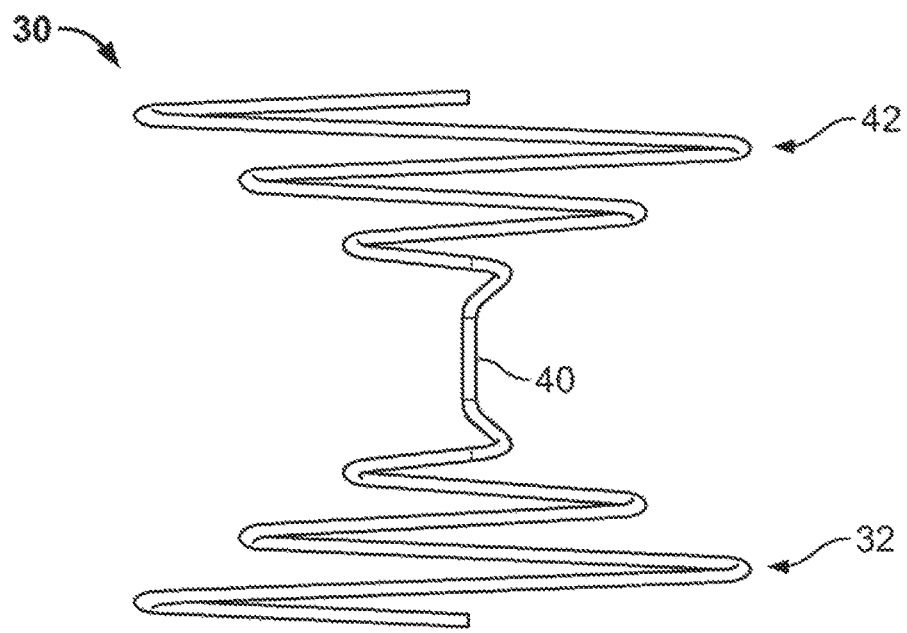
FIG. 5 shows a side view of the heart valve assisting device of FIG. 4.

FIG. 4 shows a second embodiment of a heart valve assisting device 30. The device 30 comprises a first or lower section 32, a second or upper section 42, and a connector 40 connecting the first section 32 and the second section 42. The first section 32 has a generally spiral shape, defined by the wire structure of the first section 32 forming a winding around a center 34 of the first section. The winding gradually moves away from the center 34 as it winds around the center 34. In the case of device 30, the winding of the first section 32 moves outward from the center 34 at a generally constant rate, thereby forming a substantially circular shape (in top view), while at the same time the winding moves downward from its starting point at the center, thereby forming a substantially conical helix opening downward, with the base of the cone below the vertex. The second section 42 also has a generally spiral shape, and is formed as a substantially conical helix opening upward, with the base of the cone above the vertex, similar in shape and size to the first section 32 (but a mirror image thereof).

The winding structure of the first section 32 forms a path 38 that starts from an opening 36 at the outer periphery of the spiral and that moves toward the center 34 of the spiral as the path 38 winds around the center 34 of the spiral. The winding structure of the second section 42 forms a path 48 that starts from an opening 46 at the outer periphery of the spiral and that moves toward the center 44 of the spiral as the path 48 winds around the center 44 of the spiral.

The device 30, like the device 10, is comprised of a wire having a circular cross-section. The wire of device 30 is a suitable shape memory metal, for example nitinol.

As would be understood by persons of ordinary skill in the art from the above descriptions, alternative embodiments of the device 30 may be formed, using the variations described above with respect to the device 10. Thus, for example, the first section 32, the second section 42, and the connector 40 may comprise other forms, shapes, sizes and/or materials as described above with respect to the device 10. The ends of the device may be rounded, squared-off, pointed, and/or may have anchoring elements. The first section 32 and/or the second section 42 may have one or more anchoring elements, such as barbs or hooks and/or loops to facilitate suturing. The first section 32, the second section 42, and/or the connector 40 may have one or more grooves and/or holes, as described above. The device may comprise a coating, as described above.

FIGS. 6-11 illustrate various steps in the implantation of the device 10 for repairing the functioning of a heart valve. The procedure is illustrated with respect to a mitral valve, but the procedure may also used to apply the device to a tricuspid valve.

Figure 6:
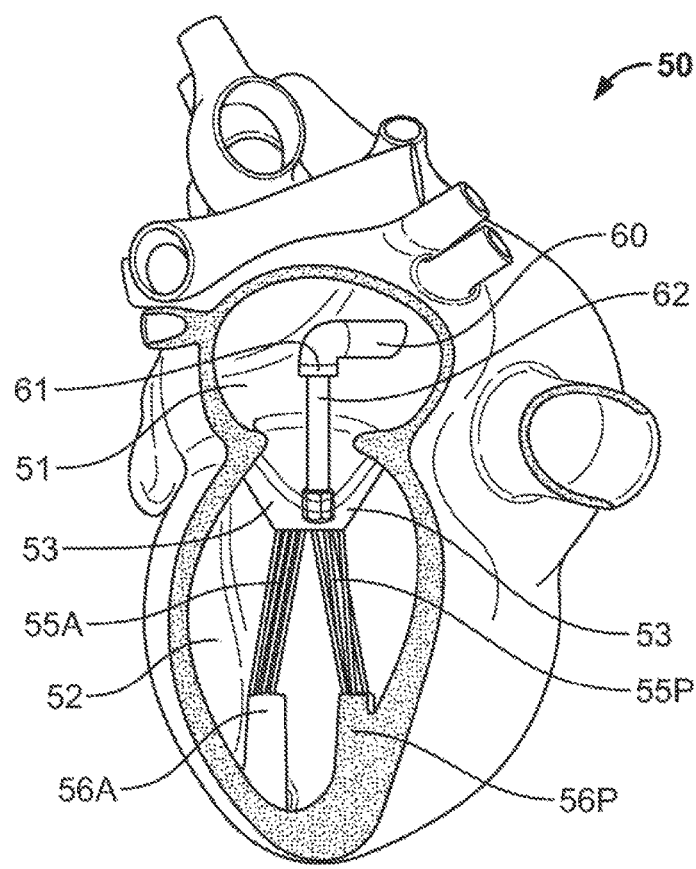
FIG. 6 shows a step in the implantation of a device for repairing the functioning of a heart valve.

FIG. 6 shows a heart 50 with a sectional view of the left atrium 51 and left ventricle 52. The mitral valve leaflets 53 are positioned between the left atrium 51 and the left ventricle 52. As is known in the art, the leaflets 53 are connected by anterior chords 55A and posterior chords 55P to anterior papillary muscle 56A and posterior papillary muscle 56B, respectively.

In the initial step of implanting the device 10, a delivery system comprising a catheter for delivering the device is positioned adjacent the valve by a method known in the art. The approach may be, for example, a transseptal approach, with the catheter entering the left atrium 51 through the septum between the right atrium and left atrium, as is shown in FIG. 6. FIG. 6 shows the tip 61 of a guide catheter 60 that has been delivered to the left atrium using a transseptal approach over a guidewire and tapered dilator. To facilitate a transseptal approach, the delivery system may include an atrial septum dilator. Other approaches alternatively may be used, including, for example, a transfemoral approach through the femoral artery and through the aorta and left ventricle into the left atrium, a transapical approach through the heart wall at the heart apex into the left ventricle, or a transatrial approach through the heart wall into the left atrium.

Once the guide catheter 60 is adjacent the heart valve, the tip 61 of the guide catheter may be moved and/or turned so that it is facing the heart valve leaflets 53. FIG. 6 shows the tip 61 turned 90 degrees toward the leaflets 53 of the mitral valve. In the illustrated method, the end of the delivery catheter 62 is advanced through the mitral valve into the left ventricle, as shown in FIG. 6. The end of the delivery catheter 62 is positioned such that it can deliver the first section 12 of the device 10 on the ventricular side of the heart valve.

Figure 7:
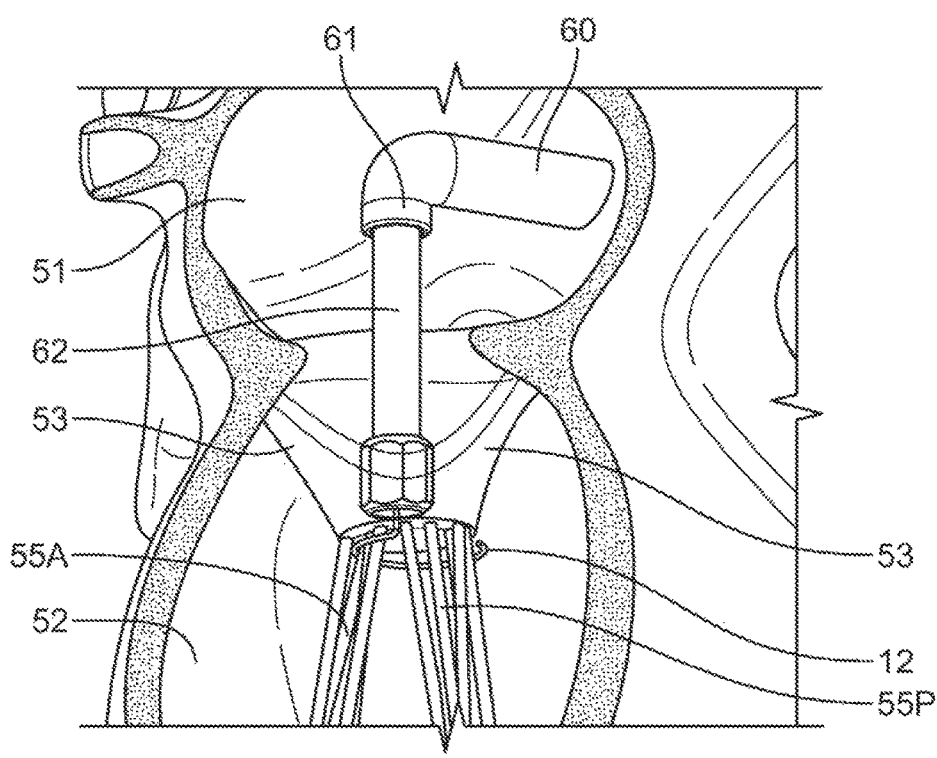
FIG. 7 shows a further step in the implantation of a device for repairing the functioning of a heart valve.

Once the end of the delivery catheter 62 is positioned in this manner, the device 10 is delivered from the delivery catheter 62, such as by a suitable pushing mechanism as is known in the art. The device 10, because it is made of a shape memory metal or other suitable material, can fit within the catheter 62 prior to being ejected from it. For example, the wire of the device 10 may be deformable to a substantially straight configuration in which it remains until ejected from the delivery catheter 62. Due to the shape memory characteristics of the device 10, once it is delivered from the delivery catheter 62, it returns to its memorized shape such as that shown in FIG. 1. Thus, as the first section 12 of the device 10 is slowly released from the delivery catheter 62, the first section 12 begins to assume its spiral shape. As shown in FIG. 7, because the delivery catheter 12 is positioned to push the first section 12 of the device 10 from the delivery catheter 12 to the ventricular side of the heart valve adjacent the chords 55A, 55P, the spiral of the first section 12 begins to wind around some, many or all of the chords 55A, 55P as the device 10 is ejected from the delivery catheter 62. The winding of the spiral may be accomplished by the spiral returning to its memorized shape upon being ejected from the delivery catheter and/or by the physician turning the device, for example by a grasping mechanism or by turning the delivery catheter itself.

While the illustrated version shows the device 10 initially positioned inside the delivery catheter 62, in an alternative embodiment the device 10 may be positioned around the outside of the delivery catheter 62. For example, the first section 12 and second section 22 may be wound around the outside surface of the delivery catheter 62. The device 10 may stay in place on the outside of the delivery catheter 62 by its own shape or by a holding element such as a sheath or suture that can be removed for delivery of the device 10.

In approaches in which the delivery catheter 62 approaches the heart valve from the atrial side (e.g., in transseptal and transatrial approaches), the device 10 may be positioned in or on the delivery catheter 62 with the first section 12 of the device 10 closer to the distal end of the delivery catheter 62. In this way, the delivery catheter 62 can be advanced from the atrium to the ventricle for delivery of the first section 12 on the ventricular side of the valve, and thereafter the delivery catheter 62 can be withdrawn back to the atrium for delivery of the second section 22 on the atrial side of the valve (as described further below). In approaches in which the delivery catheter 62 approaches the heart valve from the ventricular side (e.g., in transfemoral and transapical approaches), the device 10 may be positioned in or on the delivery catheter 62 with the second section 22 of the device 10 closer to the distal end of the delivery catheter 62. In this way, the delivery catheter 62 can be advanced from the ventricle to the atrium for delivery of the second section 22 on the atrial side of the valve, and thereafter the delivery catheter 62 can be withdrawn back to the ventricle for delivery of the first section 12 on the ventricular side of the valve. Other variations are of course possible.

Figure 8:
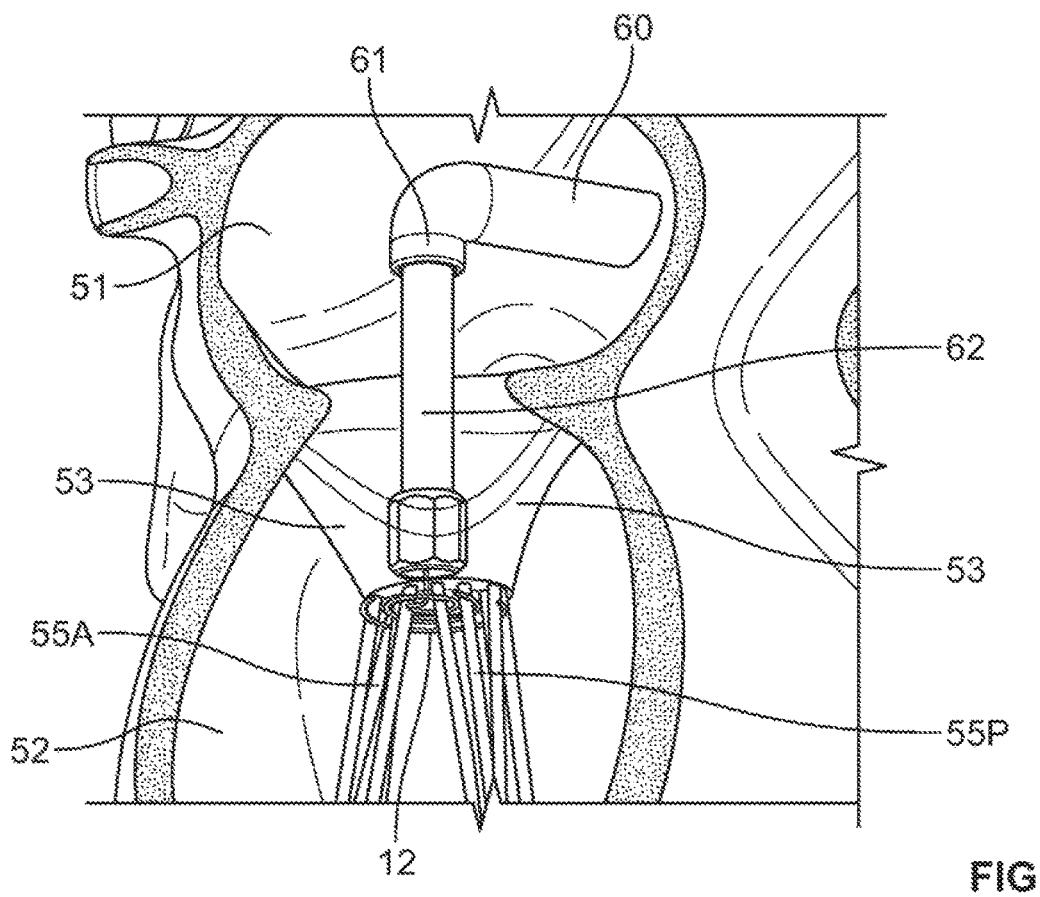
FIG. 8 shows a further step in the implantation of a device for repairing the functioning of a heart valve.

FIG. 8 shows the first section 12 fully discharged from the delivery catheter 62 (part of the spiral structure is shown in section in FIG. 8). As can be seen, the spiral of the first section 12 has wound around most of the chords, including both anterior chords 55A and posterior chords 55P. Thus, as shown in FIG. 8, the first section 12 is positioned on the ventricular side of the heart valve such that chords associated with the heart valve are positioned within the path 18 of the generally spiral shape of the first section 12.

As the first section 12 is being ejected from the delivery catheter 62, it winds in the same direction as its spiral. Thus, as explained above, and as can be seen in the top view of FIG. 2, the spiral of the first section 12 can be considered as being wound in a clockwise direction when viewed from the top and starting from the center and moving outward. As the first section 12 is being ejected from the delivery catheter, it winds in a clockwise direction when viewed from the top. Chords 55A associated with the anterior papillary muscle and chords 55P associated with the posterior papillary muscle are positioned within the path 18 of the generally spiral shape of the first section 12. Because the first section 12 undergoes winding as it is being ejected, as the first section winds around the chords 55A, 55P, the spiral shape forces the chords 55A, 55P within the path 18 closer to the center 14 of the first section 12. In this manner, the anterior chords 55A and posterior chords 55P are forced closer together, thereby reducing a gap between chords 55A associated with the anterior papillary muscle and chords 55P associated with the posterior papillary muscle.

If desired, after pushing the first section 12 of the device 10 from the delivery catheter 62, the physician may pull the first section 12 of the device 10 adjacent the heart valve. Thus, the delivery system, which includes the delivery catheter 62, may include a grasping element that can pull the device 10 in order to pull the first section 12 closer to the leaflets 53.

Figure 9:
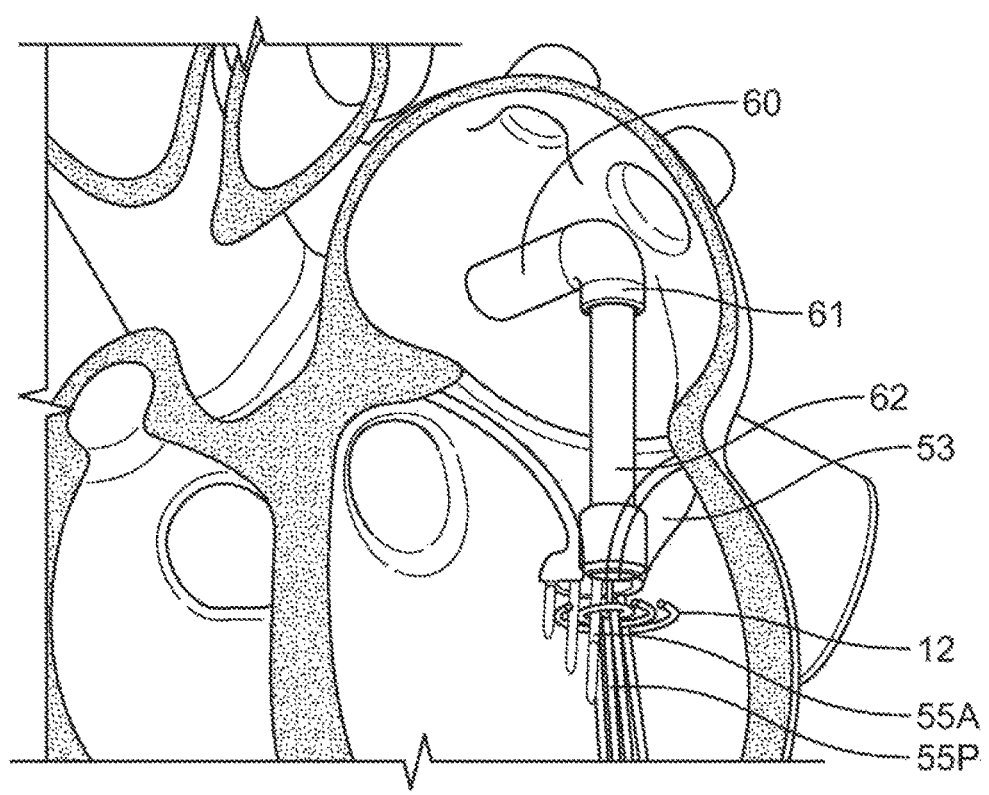
FIG. 9 shows a further step in the implantation of a device for repairing the functioning of a heart valve.

With the first section 12 positioned with some, most or all of the chords 55A, 55P within the spiral of the first section, the physician may then further turn the first section 12, in this example in a clockwise direction when viewed from the top. This may be accomplished, for example, by turning the delivery catheter 62 itself and/or by a grasping mechanism within the delivery catheter 62 that can grasp and turn the device 10. This step of turning the first section 12 forces the chords that are located within the path 18 of the spiral of the first section 12 to move closer to the center 14 of the first section 12. In this manner, the anterior chords 55A and posterior chords 55P are forced closer together. By doing this, because the chords are attached to the leaflets 53, the leaflets 53 are brought closer together. FIG. 9 shows the first section 12 after such turning, showing the chords that are located within the path 18 as having been moved closer to the center 14 of the first section 12, and also showing the leaflets 53 as having been brought closer together.

In order that the spiral of the first section may be turned to move the chords in this manner and may hold the chords, the device or at least the first section should have sufficient stiffness such that the spiral shape is generally maintained. Thus, device should be sufficiently rigid so as to maintain the spiral shape on its own and under the forces applied to it by the chords.

In alternative embodiments in which the first section comprises more than one spiral, the device may be formed so that it can gather and move the chords with fewer rotations. Thus, for example, with the first section comprising multiple spirals and with the openings for the spirals positioned at different places around the perimeter of the first section, chords at different places around the perimeter of the first section may be gathered simultaneously and moved toward the center simultaneously.

Figure 10:
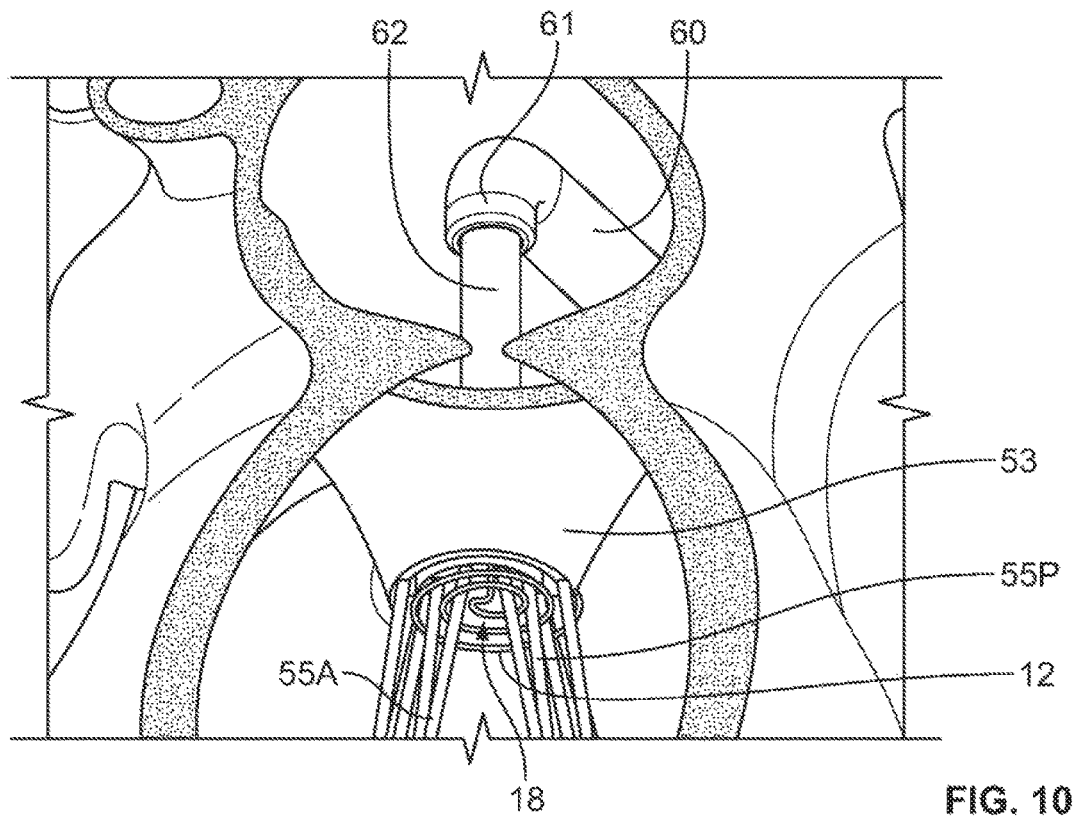
FIG. 10 shows a further step in the implantation of a device for repairing the functioning of a heart valve.

In order to adjust the device, after the physician has turned the first section 12 in a first direction as described above, the physician may turn the first section 12 back in the opposite direction in order to allow the chords to move apart by some amount. Thus, in this example, after the positioning of FIG. 9 resulting from clockwise turning, the physician may turn the first section 12 counterclockwise (when viewed from the top) in order to allow the chords 55A, 55P to move away from the center 14 of the first section 12, thereby allowing them to separate by some distance. The physician can monitor the positioning of the chords 55A, 55P and leaflets 53 and turn the first section 12 clockwise or counterclockwise as needed in order to obtain the desired result. FIG. 10 shows the device 10 after some counterclockwise movement in relation to FIG. 9.

If desired, after the first section 12 has been rotated into the desired rotational position, the physician may pull the first section 12 of the device 10 adjacent the heart valve. As described above, this may be accomplished by using a grasping element that can pull the device 10 in order to pull the first section 12 closer to the leaflets 53.

Figure 11:
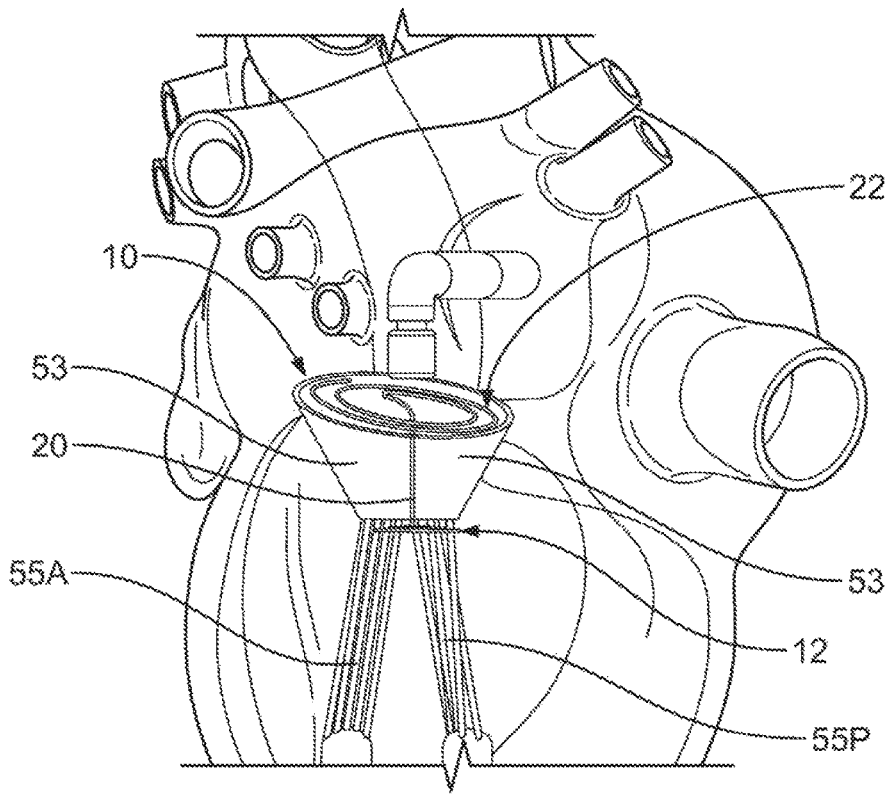
FIG. 11 shows a further step in the implantation of a device for repairing the functioning of a heart valve.

When the first section 12 is in the desired position, the remainder of the device 10 is ejected from the delivery catheter 62, as shown in FIG. 11. This can be accomplished by withdrawal of the tip of the delivery catheter 62 toward the left atrium. In some embodiments, a pusher also may be used to force the remainder of the device 10 from the delivery catheter 62.

When ejected, the second section 22 is positioned on an atrial side of the heart valve. The second section 22 is shaped and dimensioned so as to hold the device in place. Thus, the wide second section 22 can be held by the annulus of the valve and/or adjacent tissue of the wall of the atrium. If desired, anchoring elements may be provided. For example, barbs or hooks may be formed on the second section 22, and/or the second section 22 may be provided with one or more loops to facilitate suturing the second section 22 in place. A suture may be used as an anchoring element, with or without one or more loops on the second section 22. The anchoring elements (e.g., barbs, hooks, loops, sutures, etc.) may be placed at the end of the spiral, along the outer wind of the spiral, and/or at any other suitable position, in order to assist in maintaining the positioning of the device.

It will be appreciated that in approaches in which the delivery catheter 62 approaches the heart valve from the ventricular side (e.g., in transfemoral and transapical approaches), similar methods as described above and illustrated in FIGS. 6-11 may be used, modified to account for the fact that the delivery catheter approaches the valve from the opposite side. Thus, as mentioned above, the device 10 may be positioned in or on the delivery catheter 62 with the second section 22 of the device 10 closer to the distal end of the delivery catheter 62 than the first section 12. In one example, with the device 10 positioned on the outside of the delivery catheter 62, the delivery catheter 62 first can deliver the first section 12 on the ventricular side of the valve, and the chords may be captured as described above. Thereafter, the delivery catheter 62 can be advanced from the ventricle to the atrium for delivery of the second section 22 on the atrial side of the valve, as described above. In an alternative example, the delivery catheter 62 first can be advanced from the ventricle to the atrium for delivery of the second section 22 on the atrial side of the valve. Thereafter, the delivery catheter 62 can be withdrawn back to the ventricle, and the first section 12 can be delivered on the ventricular side of the valve for capturing the chords.

As would be understood by persons of ordinary skill in the art from the above descriptions, alternative embodiments of the device 10 and/or the device 30 may be implanted generally as described above. The method of implantation may be varied as appropriate with respect to the particular embodiment used and the particular patient being treated.

Figure 12:
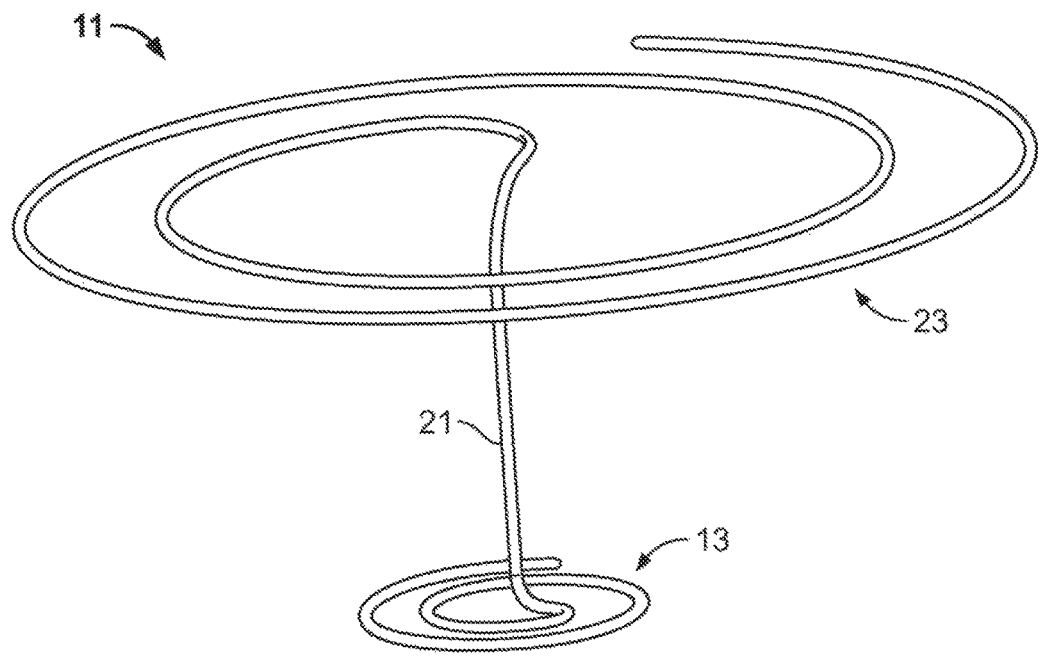
FIG. 12 shows a perspective view of another embodiment of a heart valve assisting device.

As described above, in the device 10 of FIGS. 1-3, both first section 12 and second section 22 have windings in the same direction. In an alternative embodiment, the spiral of the second section can be wound in an opposite direction from that of the spiral of the first section. An example of such an embodiment is shown in FIG. 12, which shows a device 11 comprising a first section 13, a second section 23, and a connector 21. As can be seen in FIG. 12, the spiral of the second section 23 is wound in an opposite direction from that of the spiral of the first section 13. The end of the second section 23 can press into heart tissue or have an anchoring element formed in such a way that the second section 23 is more easily rotated in one direction (in which the end of the winding is the trailing end of the movement) than in the other direction (in which the end of the winding is the leading end of the movement). Thus, if the first section 13 and the second section 23 are wound in opposite directions as in the device 11, the turning of the first section 13 to draw the chords closer together can be accompanied by a relatively easy rotation of the second section 23. However, the second section 23 can resist rotation in the opposite direction. In this way, the device 11 can resist unwinding.

Other mechanisms for resisting unwinding include anchoring elements as described above as well as the use of different shapes. For example, if the first section 12 is in an elliptical shape, the chords will tend to gather in the apices of the long axis of the ellipse. In order for the device to rotate, the chords would need to be drawn closer together, which is a movement they would tend to resist. Accordingly, such an elliptical shape can assist in preventing an unwanted rotation of the device.

The second section, positioned on an atrial side of the heart valve, stabilizes the location of the device, with or without the use of anchoring elements. Tissue can grow around the second section, and the anchoring elements (if used) and/or tissue fixation allows the device to hold the diameter of the annulus and prevent annulus dilatation.

Figure 14:
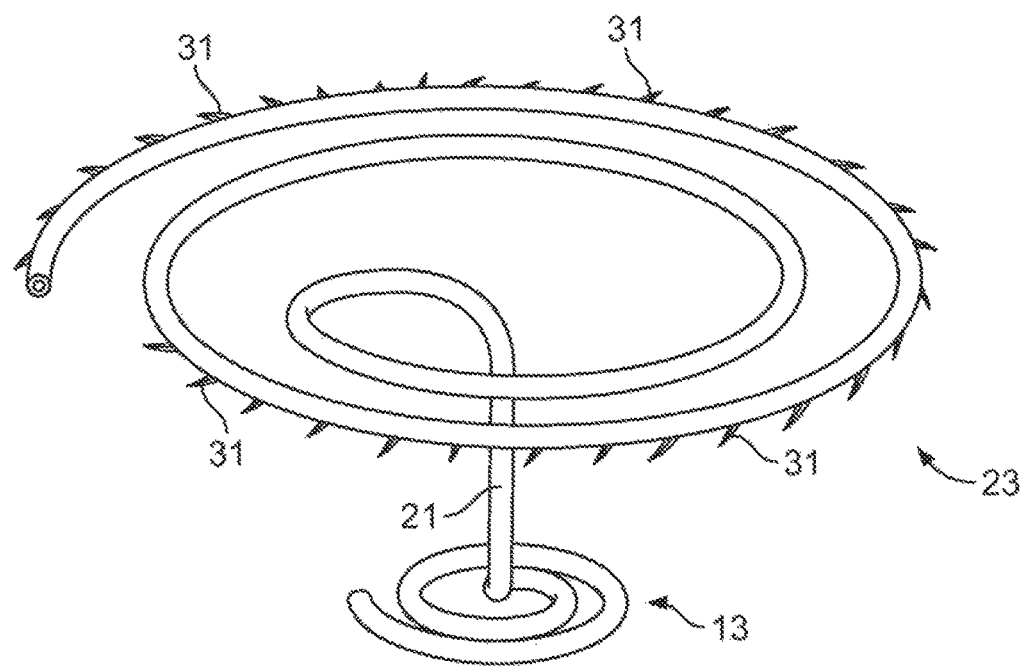
FIG. 14 shows a perspective view of another embodiment of a heart valve assisting device.

FIG. 14 shows an embodiment in which a plurality of anchoring elements in the form of barbs 31 are provided for anchoring the second section 23. The barbs 31 may be oriented in a direction to allow relatively free rotation of the device in one direction (e.g., clockwise when viewed from the top, corresponding to bringing the chords to the center) but to resist rotation of the device in the opposite direction (e.g., counterclockwise when viewed from the top, corresponding to loosening of the chords). That is, the barbs 31 may be angled so as to slide over tissue in the first direction but to press into tissue in the opposite direction. In an alternative variation, the second section may be a tube with holes for the anchoring elements, and the anchoring elements may be located on a wire located within the tube, such that the anchoring elements may be extended or retracted through the holes by manipulating the wire. As mentioned above, the anchoring elements may take various forms, such as barbs, hooks, loops, sutures, etc.

As also mentioned above, one or more grooves, holes and/or coatings may be provided to facilitate and/or stimulate tissue growth in and/or around the second section to anchor the second section. When the second section is anchored to the annulus, whether by anchoring elements or tissue growth or other means, the second section can hold the diameter of the annulus and prevent annulus dilatation, thereby maintaining the functioning of the heart valve.

When a device as described is placed in position as described, the spiral of the first section reduces a gap between chords associated with the anterior papillary muscle and chords associated with the posterior papillary muscle. In this manner, the leaflets of the valve are drawn closer together. In some instances, the control of the chords also can reduce the movement of the leaflets, in order to help prevent prolapse. The control of the chords and the drawing of the leaflets closer together facilitate coaptation of the leaflets, such that they can close together sufficiently to correct the regurgitation issue. The device can be left in place as a long-term treatment.

Figure 13:
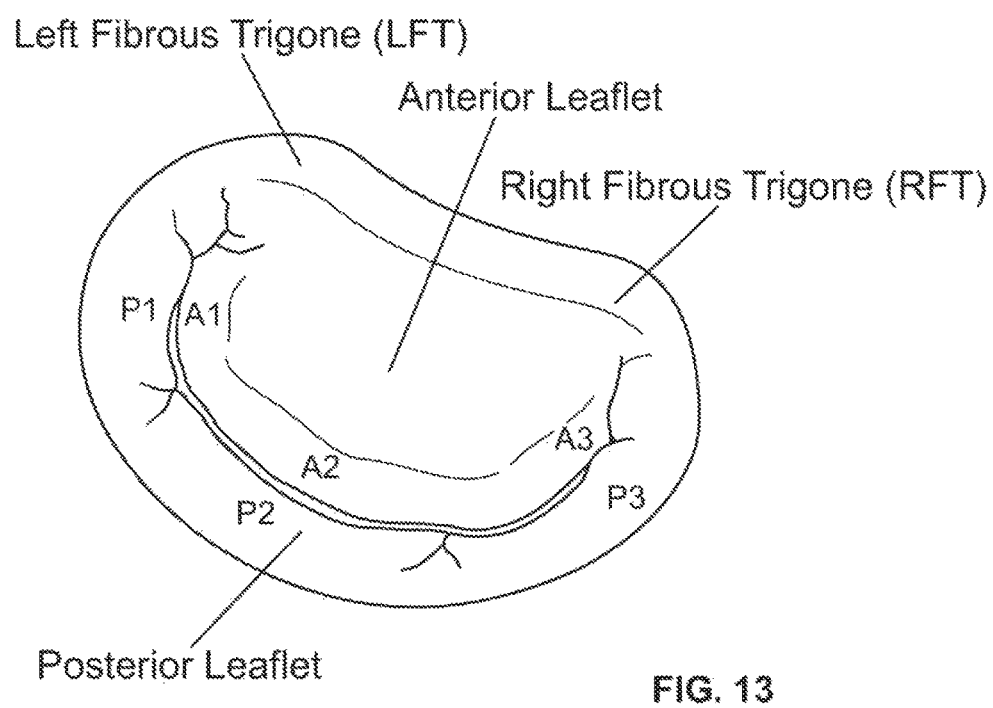
FIG. 13 shows a top view of mitral valve leaflets.

FIG. 13 shows a top view of leaflets of a mitral view. A device as described may be used in various positions and for gathering various chords. For example, the device may be positioned approximately in the area of A2 and P2 near the center of the anterior and posterior leaflets. The chords on A2 and P2 are trapped and gathered by the spiral(s) of the first section. A rotation of the spiral would eventually bring all such chords to the same location, which is the spiral center. In this situation, the gap between A2 and P2 could be brought to zero. Rotating the spiral a little less would result in a narrow gap. The device alternatively may be positioned approximately in the area of A1 and P1, in which case the chords on A1 and P1 are trapped and gathered by the spiral(s) of the first section, reducing the distance between A1 and P1. The device alternatively may be positioned approximately in the area of A3 and P3, in which case the chords on A3 and P3 are trapped and gathered by the spiral(s) of the first section, reducing the distance between A3 and P3. A device with a large spiral positioned approximately in the area of A2 and P2 may trap and gather chords on A2, P2, A1, P1, A3 and/or P3, and can be used to reduce the distance between P1 and P3, for example, or A1 and A3.

In some instances, it may be desired to use the device to draw the leaflets closer and then position a clip anchored to both leaflets or stitch or suture the leaflets together. Thus, the device in conjunction with one or more clips, stitches or sutures can facilitate coaptation of the leaflets.

If desired, the device may be adjusted or withdrawn at a later time, either shortly or long after the implantation. A catheter may be used to access the device. Its anchoring elements, if any, may be released. To adjust the device, the physician may turn the spiral of the first section as described above (e.g., by turning the device) in order to bring the chords closer together or to allow them to separate further apart, as desired. Thus, the turning may be done while performing the initial implantation procedure and/or as an additional later procedure that is separate from the implantation procedure. In this manner, the regurgitation grade can be controlled. Alternatively, if it is desired to withdraw the device altogether, a grasping element may be used to grasp the device and pull it back into the catheter, in essentially the reverse of the procedure that was used to deliver the device.

Numerous alternatives are possible within the scope of the invention. For example, as mentioned above, the winding of the spiral may move away from the center at a non-constant rate. Thus, the spiral density need not be constant. In an alternative embodiment for the second section, for example, the second section may have one or more close turns near the center, then one or more wide turns, then one or more close turns again near the outer perimeter. The inner turns can reduce the potential for leaflet prolapse, by providing a stop that can prevent the leaflets from movement into the atrium. In the event of one or more torn chords, the leaflet(s) might have a greater tendency for prolapse into the atrium. Thus, the inner turns can help prevent such prolapse. The outer turns provide the outer annulus stabilizing function (as described above).

In another variation, an adjustable connector can be used. During and/or after implantation, the physician may desire to adjust the distance, radial orientation and/or axial orientation between the first section and the second section. For this purpose, the connector can include a mechanism that allows adjustment of the distance and/or orientation between the first section and the second section and that allows the sections to be fixed in a specific state once the physician decides that their mutual location is satisfactory. In one example, the first section and second section can be joined by a connector having a changeable length, thereby providing the ability to move the first and second sections closer together or farther apart. The connector length may be adjustable by the connector having a telescopic mechanism, a screwing mechanism, or any other suitable mechanism. With this adjustable connector, the device can be adjusted to a specific mitral valve size. Moreover, moving the first and second sections closer together after they are positioned on opposite sides of the valve results in further fixation of the two leaflets against each other to improve coaptation.

Figure 15:
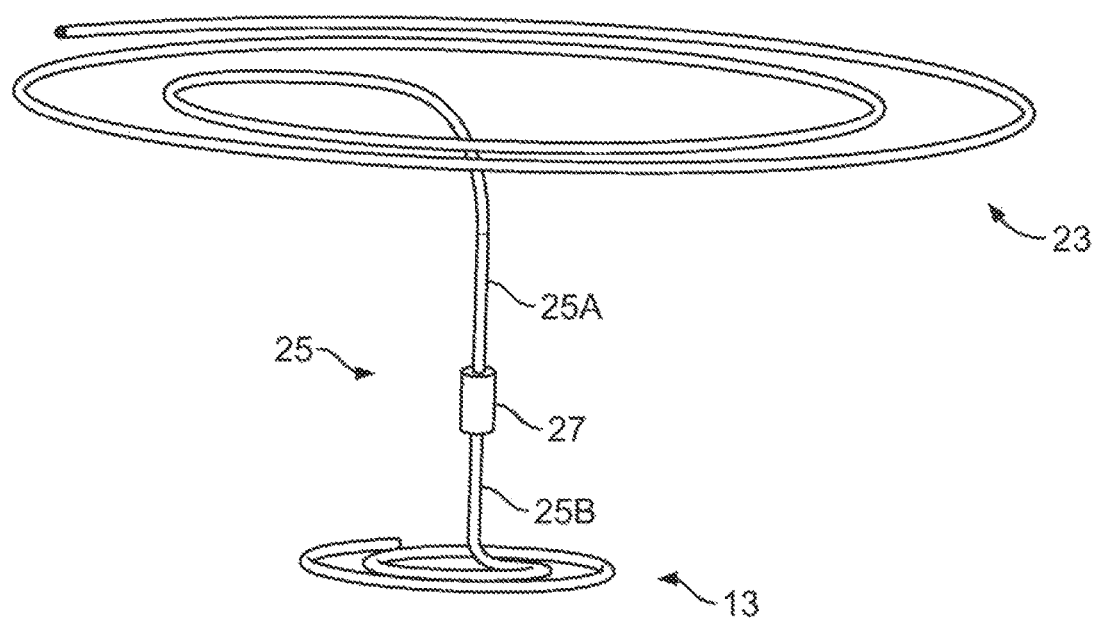
FIG. 15 shows a perspective view of another embodiment of a heart valve assisting device.

FIG. 15 shows an embodiment with a connector 25 that allows adjustment of the distance and orientation between the first section 13 and the second section 23. The connector has an upper part 25A and a lower part 25B. A locking element 27 may be used to lock or unlock the lower part 25B with respect to the upper part 25A. When the device is generally in position, the locking element 27 may be actuated (e.g., by turning or sliding, similar to known locking mechanisms) to unlock the lower part 25B with respect to the upper part 25A. The distance between the first section 13 and the second section 23 and/or the angular orientation of the first section 13 relative to the second section 23 may be adjusted in order to suit the patient's physiology and/or in order to obtain the desired tension in the chords. Then the locking element 27 may again be actuated to lock the lower part 25B with respect to the upper part 25A.

In another variation, a hollow connector may be used as an open port to access the ventricle following the implantation. For example, a tubular connector allows a direct access to the center of the first section (located in the ventricle), permitting access to adjacent points of the anterior and posterior leaflets. This type of connector, especially if it has a known definitive geometry, may serve as an access point for the implantation of another device that attaches the leaflets themselves. In order to eliminate back-flow of blood from the ventricle to the atrium, the tubular passage of the connector may be closed or configured to automatically close when not in use.

Figure 16A:
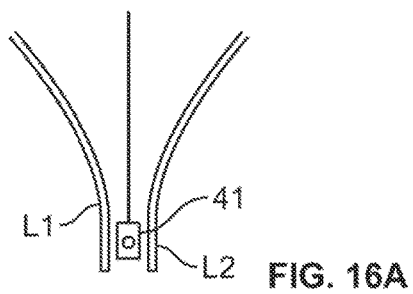
FIG. 16A shows a side view of a connector for a heart valve assisting device.
Figure 16B:
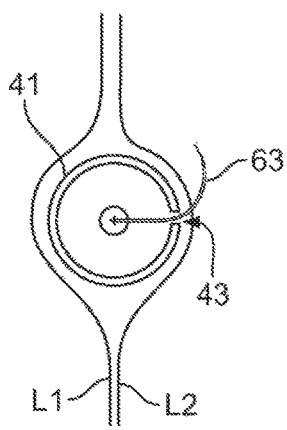
FIGS. 16B-16D show steps in deploying a fixation element from the connector of the heart valve assisting device.
Figure 16C:
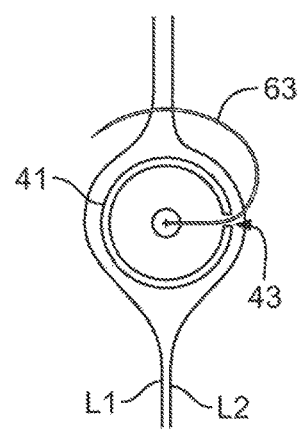
Figure 16D:
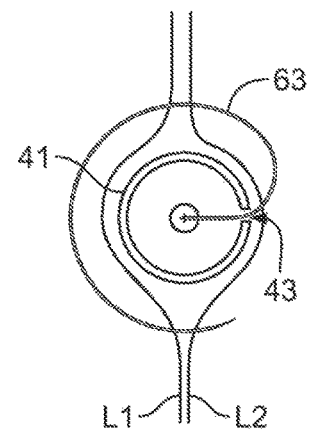

FIGS. 16A through 16D illustrate deployment of a fixation element from a tubular connector of a device as described above. As will be appreciated from the above-described implantation procedure, when the device is implanted, the first section is positioned on the ventricular side of the valve, the second section is positioned on the atrial side of the valve, and the connector extends through the valve between the leaflets. FIG. 16A shows a side view of a hollow connector 41 between leaflets L1 and L2, and FIGS. 16B-16D show cross-sectional views of the hollow connector 41 between leaflets L1 and L2. As can be seen in these figures, the hollow connector 41 has at least one opening 43 through which one or more fixation element(s) 63 may be deployed. The fixation element(s) 63 may be one or more sutures, staples, tacks, threads, wires, bands or other suitable fixation element(s) and may be constructed out of any suitable material, such as a shape memory material (e.g., nitinol) or other material. In FIGS. 16B-16D, the fixation element 63 is a nitinol suture that takes a generally circular or spiral shape as it is deployed from the connector 41. When the fixation element 63 is first advanced from the connector 41, as shown in FIG. 16B, it pierces the leaflet L2. As the fixation element 63 is further advanced from the connector 41, as shown in FIG. 16C, it then pierces the leaflet L1. As the fixation element 63 is further advanced from the connector 41, as shown in FIG. 16D, it again pierces the leaflet L2. In this manner, the leaflets L1 and L2 are attached to each other and to the connector 41.

Figure 17A:
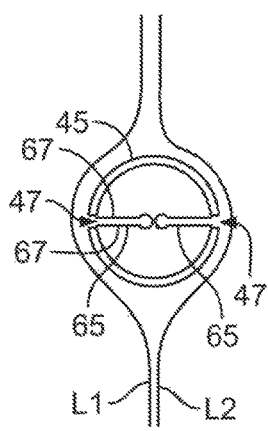
FIGS. 17A-17C show steps in deploying another embodiment of fixation elements from the connector of a heart valve assisting device.
Figure 17B:
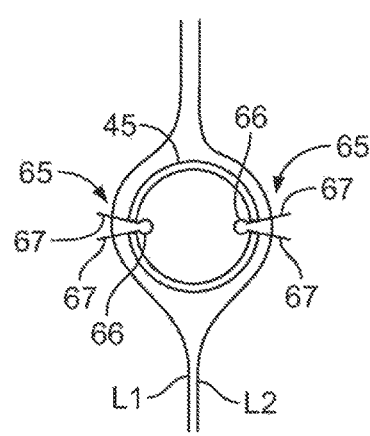
Figure 17C:
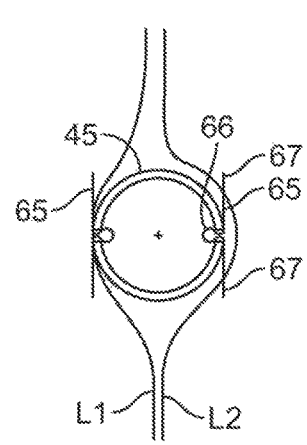

FIGS. 17A through 17C illustrate deployment of another embodiment of fixation elements from a tubular connector of a device as described above. FIG. 17A-17C show cross-sectional views of a hollow connector 45 between leaflets L1 and L2. As can be seen in these figures, the hollow connector 45 has at least one opening 47 through which one or more fixation element(s) 65 may be deployed. The fixation element(s) 65 in this embodiment are in the form of nitinol tacks that take the shape as shown in FIG. 17C when deployed from the connector 45. Each tack 65 is shown as having a head 66 and prongs 67. As shown in FIG. 17A, prior to deployment the prongs 67 of the fixation elements 65 are held in a closed position within the connector 45. As the fixation elements 65 are advanced from the connector 45, they begin to open, and the prongs 67 of the tacks 65 pierce the leaflets L1 and L2, as shown in FIG. 17B. When fully deployed, as shown in FIG. 17C, the prongs 67 hold the leaflets L1 and L2, and the heads 66 are held by the connector 45, because the heads 66 are larger than the openings 47 and thus cannot fit through the openings 47. In this manner, the leaflets L1 and L2 are attached to each other and to the connector 45.

Figure 18:
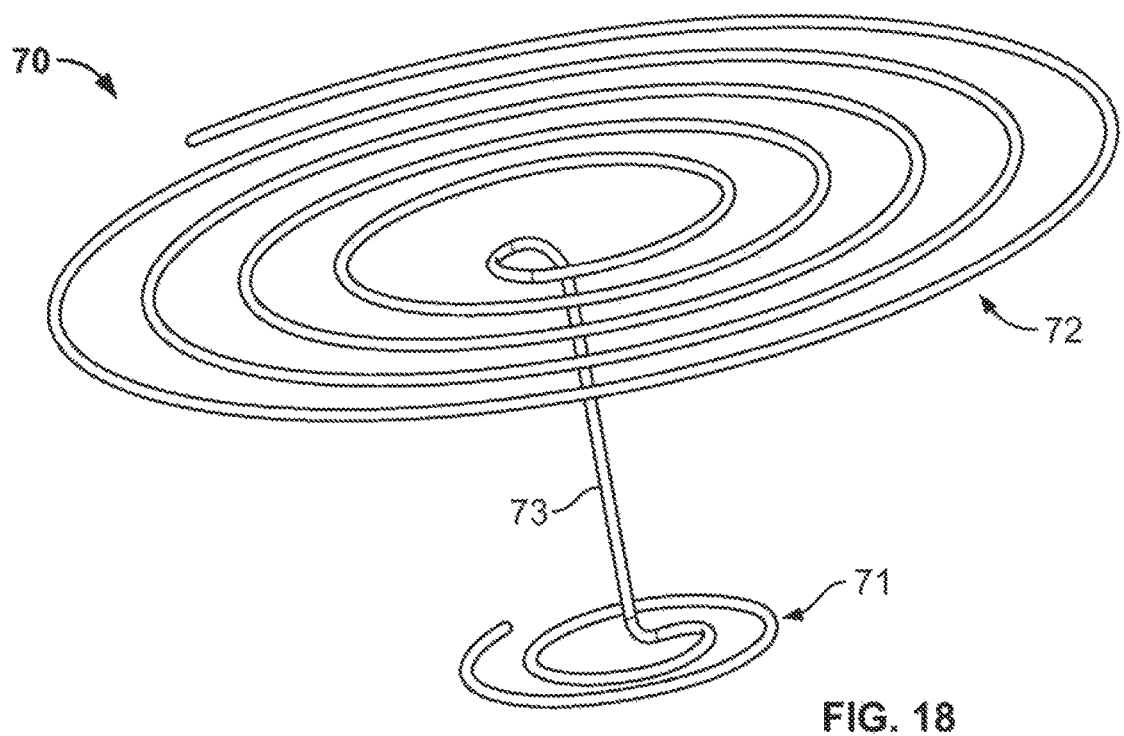
FIG. 18 shows a perspective view of another embodiment of a heart valve assisting device.

FIG. 18 shows an alternate form of a heart valve assisting device 70 sharing similarities with the devices 10, 11 and 30 described above. The device 70 comprises a first or lower section 71, a second or upper section 72, and a connector 73. This device 70 is similar to the device 11 except that the upper section 72 has a higher density of turns (turns per radial distance), with turns located in the central portion of the winding. This design variation can be used in order to address instances in which one or more leaflets wave into the atrium during systole (prolapse). The closely spaced turns of the inner part of the atrial spiral act as a lattice that prevents the leaflet(s) from waving towards the atrium. The device 70 may be implanted in a similar manner as described above with respect to the devices 10, 11 and 30, and variations of this device 70 may be made as described above with respect to the devices 10, 11 and 30.

Figure 19:
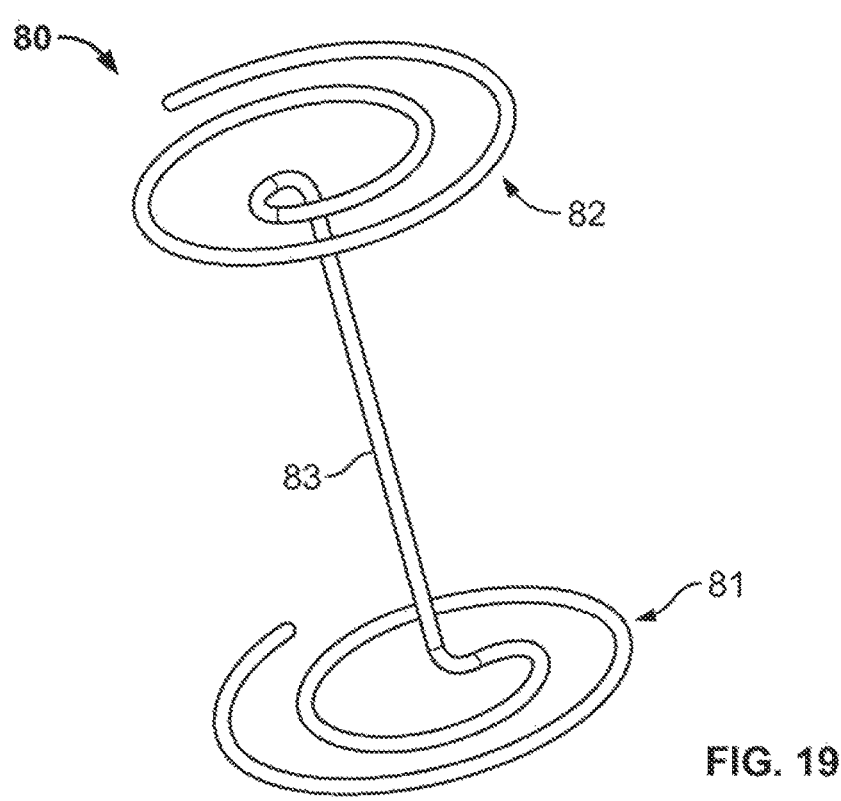
FIG. 19 shows a perspective view of another embodiment of a heart valve assisting device.

FIG. 19 shows an alternate form of a heart valve assisting device 80 sharing similarities with the devices 10, 11, 30 and 70 described above. The device 80 comprises a first or lower section 81, a second or upper section 82, and a connector 83. This device 80 is similar to the device 70 except that the upper section 82 is smaller, without the outer turns. The diameter of the upper section 82 is about the same as the diameter of the lower section 81. In this variation, the length of the connector 83 is adjustable. On implantation, the physician reduces the distance between the lower section 81 and the upper section 82, and, as a result, both the lower section 81 and the upper section 82 are squeezed against the leaflets. Because this alone can be sufficient to hold the device in place, the larger diameter portion of the upper section as shown in the devices 10, 11, 30 and 70 is omitted from the device 80. The device 80 may be implanted in a similar manner as described above with respect to the devices 10, 11, 30 and 70, and variations of this device 80 may be made as described above with respect to the devices 10, 11, 30 and 70.

If the device is formed as a tube, a wire or stiffening element may be placed into the tube in order to change the stiffness and/or shape of the tube or a section of it. For example, a stiffening element may be used to maintain the device in a first shape for delivery (e.g., relatively straight), and the stiffening element may be withdrawn upon delivery of the device from the delivery catheter in order to allow the device to take its implantation shape. In another example, an inner wire may be attached to the distal end of the tube, and the inner wire may be pulled relative to the tube to change the shape of the tube. Pulling the inner wire applies a compressive force to the tube. The tube may be formed with pre-shaped side cuts along the tube, such that it bends in a predetermined pattern, e.g., a spiral pattern, when such a load is applied. A locking mechanism may be used to lock the wire in its loaded position relative to the tube. Different depths and widths of the side cuts and the distance between the side cuts would determine the final shape of the tube element once a load is applied.

The device may have other elements to monitor the functioning of the device and the heart valve. For example, the device may be equipped with a sensor attached to the device. The sensor may be, for example, a pressure sensor, a temperature sensor, and/or a velocity sensor. In this way, the operation of the valve and the blood flow can be monitored. Similarly, the device itself when formed as a tube can be used as a "pig tail" for measuring pressure during or after the implantation procedure.

In one example of the use of sensors, the use of MEMS (microelectromechanical systems) sensors on the device may assist in the implantation procedure or during the years after it. Such sensors may monitor temperature, oxygen saturation, pressure, blood velocity or similar physical characteristics. During the implantation procedure, it is possible to use an xyz (positioning) sensor on the device to assist in the accurate location and positioning of the device by using an external system that reads the information transmitted from the sensor.

Sensor(s) on the device or delivery system may be part of a closed-loop system that uses the signals from the sensor(s) as feedback for automatic delivery and positioning. By using pressure sensors in the ventricle and atrium, the pressure can be continuously monitored as the device is automatically adjusted. The adjustments and monitoring can be continued until target pressure readings are achieved. This automatic positioning with the use of feedback can eliminate the need for manual monitoring and positioning that can be complicated and less accurate.

The device may also have an energy-producing element that produces energy by the flow of blood around the device and/or by the pressure changes using a converter (such as a piezoelectric element that is capable of converting mechanical pulse into electric current). The energy may charge a battery that, for example, can be used to transmit signals from one or more sensors as described above.

From the description herein, a person of ordinary skill in the art can recognize that certain embodiments of devices and methods disclosed herein can have several advantages. For example, the device can safely hold the chords without requiring grasping of the leaflets. The movement of the chords toward each other can be controlled by the structure of the device, including, for example, the number of turns of the spiral of the first section, the radii of those turns, and their shape. The second section holds the device in place and can help prevent leaflet prolapse. The connector can determine the centerline for coaptation with minimal interruption of blood flow.

As mentioned above, the upper section (placed on the atrial side of the valve) can be anchored to the annulus, by anchoring elements or tissue growth or other means, whereby the upper section can hold the diameter of the annulus and prevent annulus dilatation. In some cases, this treatment may be sufficient, and it may be desired to disconnect and remove the remainder of the device (e.g., the lower section and the connector). Thus, the device may be similar to that shown in FIG. 15, wherein the element 27 may be a disconnecting element that may be used to disconnect the lower part 25B from the upper part 25A. The disconnecting element 27 may be adjacent the upper section 23, so that substantially all of the connector 25 can be detached from the upper section 23 and removed from the heart, along with the first section 13. The second section 23 remains in the heart as an annuloplasty ring or device.

In some cases, it may be desired not only to prevent further annulus dilatation but also to repair/reconstruct the annulus, by reducing its diameter. To accomplish this, annuloplasty rings or devices may be provided that can pull the annulus toward its original physiological size.

Figure 20A:
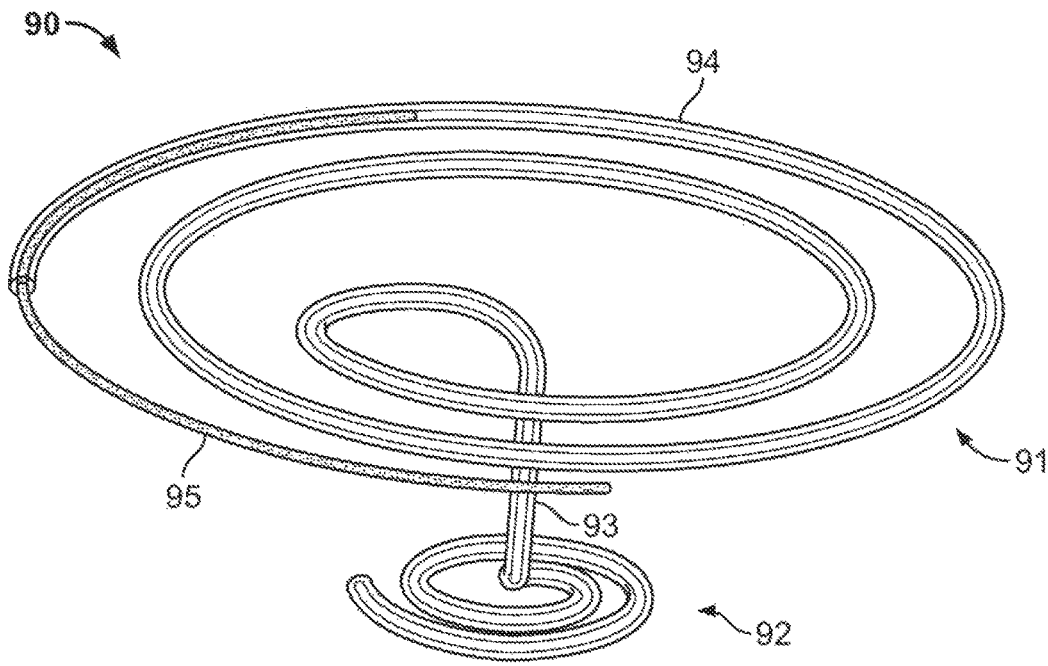
FIGS. 20A and 20B show perspective views of a device that can be used for annuloplasty.
Figure 20B:
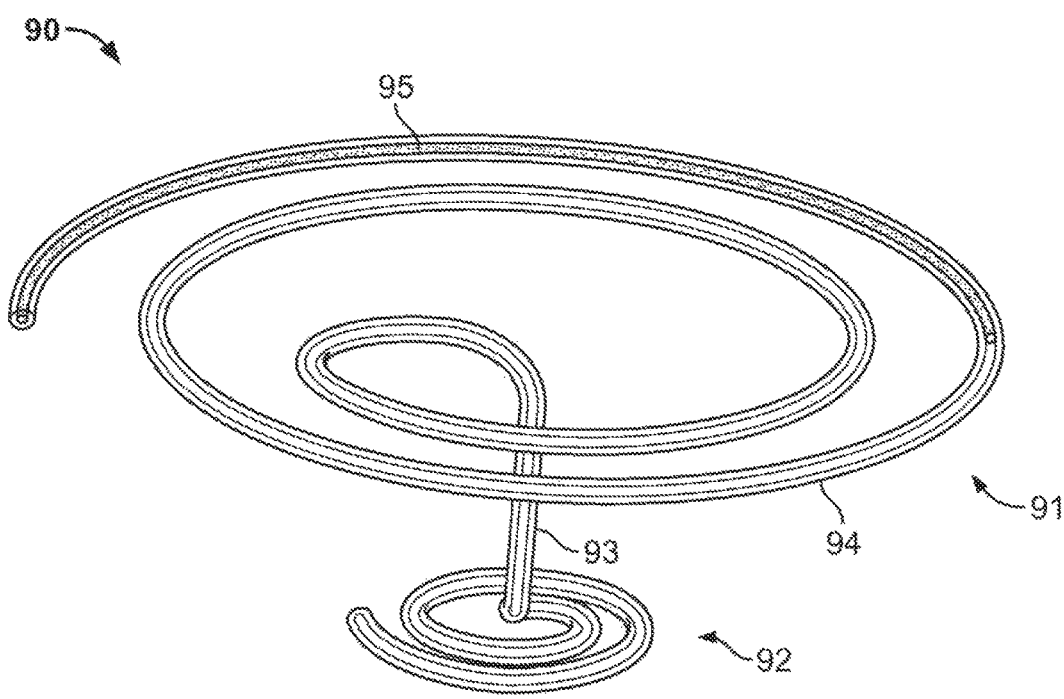

FIGS. 20A and 20B illustrate an embodiment comprising an annuloplasty ring or device 90 that can pull the annulus toward its original physiological size. As illustrated, the device 90 comprises an atrial element 91, a ventricular element 92 and a connector 93. However, it is also possible for the device 90 to be provided as only the atrial element 91 (i.e., without the ventricular element 92 or connector 93). The atrial element 91 comprises a tubular element 94 and a deflecting ring 95. When the device 90 includes a ventricular element 92 and connector 93, the device 90 may generally be implanted as described above with reference to devices 10, 11, 30, 70 and 80. Otherwise, if the device 90 is simply the atrial element 91, the physician may simply implant the device 90 such that the tubular element 94 is positioned in the atrium at the annulus. In either case, the tubular element 94 is sized so as to generally fit the size of the dilated annulus. After the tubular element 94 is anchored to tissue by suitable means (e.g., anchoring elements, tissue growth), the deflecting ring 95 is advanced into the channel of the tubular element 94. The deflecting ring 95 has a resting radius of curvature that is smaller than the resting radius of curvature of the tubular element 94, and the deflecting ring 95 has a stiffness that is selected to cause inward deflection of the tubular element 94 when the deflecting ring 95 is advanced through the tubular element 94. With the tubular element 94 anchored to the annulus, the physician advances the deflecting ring 95 along the channel of the tubular element 94, further into the tubular element 94. This causes the tubular element 94 to be deflected to a smaller diameter, as shown in FIG. 20B. This pulls the annulus toward its original physiological size.

Figure 21A:
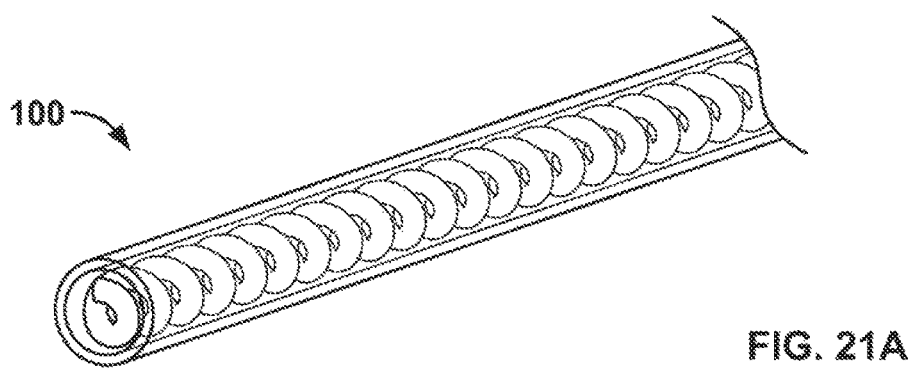
FIGS. 21A-21D show perspective views of another device that can be used for annuloplasty.
Figure 21B:
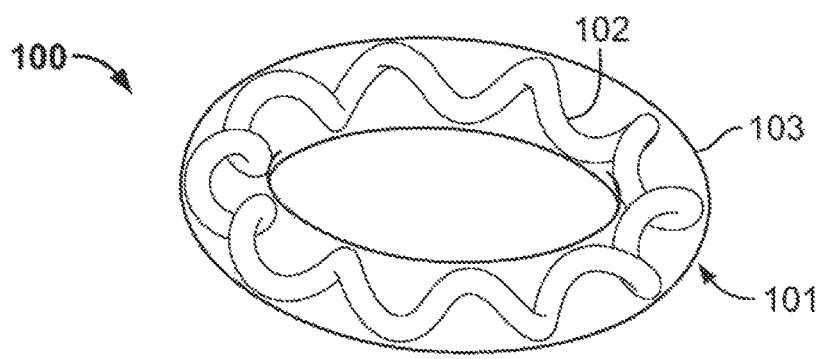
Figure 21C:
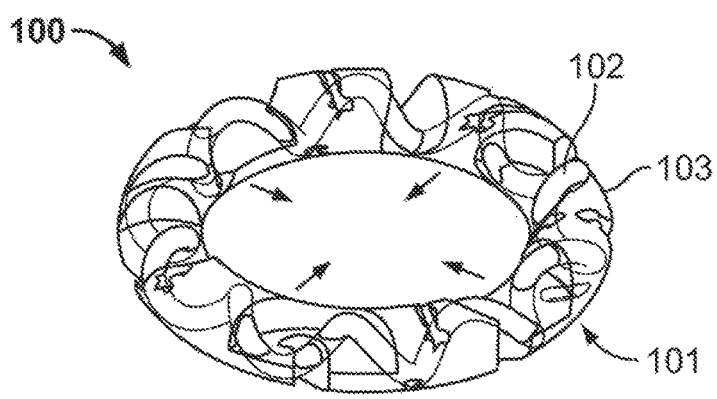
Figure 21D:
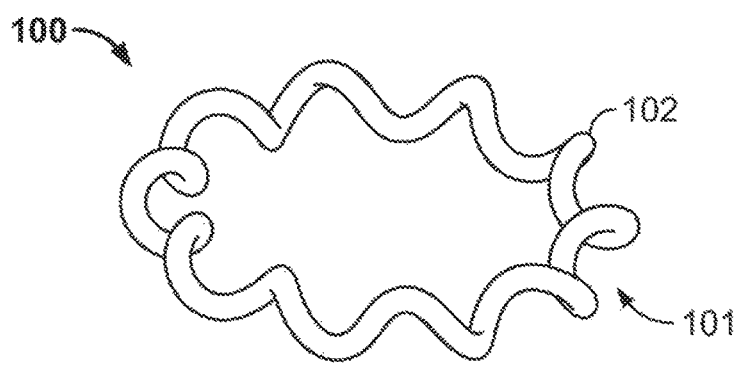

FIGS. 21A through 21D illustrate another embodiment comprising an annuloplasty ring or device 100 that can pull the annulus toward its original physiological size. As illustrated, the device 100 comprises only an atrial element 101, but it would be possible to include a ventricular element and a connector as described above. The atrial element 101 comprises a helical spring 102 covered by a biodegradable coating 103. FIG. 21A shows the atrial element 101 in a straight configuration, as it would be held inside a delivery catheter. Once advanced from the delivery catheter to the annulus, the atrial element 101 takes the ring shape as shown in FIG. 21B. The atrial element 101 is then anchored to the annulus by means as described above (e.g., anchoring elements, tissue growth). The spring 102 has a resting diameter that is smaller than that shown in FIG. 21B, but the coating 103 initially holds the spring at a larger diameter (as shown in FIG. 21B) sized to fit the dilated annulus. Over time, the coating 103, which may be a biodegradable polymer, biodegrades. As this happens, the spring 102 returns to its smaller resting diameter, as shown in FIG. 21C. With the coating gone, as shown in FIG. 21D, the spring 102 returns to a smaller diameter, as it pulls the annulus toward its original physiological size.

In another variation of an annuloplasty ring or device that can pull the annulus toward its original physiological size, the atrial element 101 may comprise a helical spring 102 that has a resting diameter sized to fit the dilated annulus. Once advanced from the delivery catheter to the annulus, the spring 102 takes a ring shape generally fitting the dilated annulus. The spring 102 is then anchored to the annulus by means as described above (e.g., anchoring elements, tissue growth). Then, to reduce the diameter of the spring 102, the physician pulls a string (or suture, wire, etc.) that is threaded through the spring 102. Upon pulling the string, the spring 102 is pulled to a smaller diameter, thereby pulling the annulus toward its original physiological size.

In another variation, one or more of the devices illustrated and/or described herein may be used as an anchoring device for holding an artificial valve. For example, the second section 22 of the device 10 may hold an artificial valve across the spiral. When the device is positioned as described herein, the artificial valve is positioned at the site of the valve in need of repair or replacement, and the artificial valve can perform the function of that valve. Similarly, the first section 12 of the device 10 may hold an artificial valve across the spiral. An artificial valve may be held not only by the first and/or second section of the device 10 illustrated in FIG. 1 but also by the first and/or second section of the other devices illustrated and/or described herein. An artificial valve may also be held by a spiral or ring as described herein that is designed for positioning only on one side of the valve being repaired or replaced, such as an atrial element 91 or 101.

Based on the above description and the accompanying drawings, the principles and operation of the invention, as well as how to make and use the invention, can be understood by persons of ordinary skill in the art. Many embodiments and variations are possible that take advantage of the principles and operation of the invention described herein. The examples described herein and shown in the accompanying drawings are meant as examples only and are not intended to be limiting of the scope of the invention defined by the appended claims.

What is claimed is:

1. A device for assisting the functioning of a heart valve comprising:
   a first section comprising a winding having an inner end and an outer end and a generally spiral shape, the winding emanating from a center of the first section and moving away from the center of the first section as it winds around the center of the first section, the first section adapted to be positioned on a ventricular side of the heart valve such that chords associated with the heart valve are positioned within the path of the generally spiral shape of the first section, the inner end of the winding being located at the center of the first section;
   a second section adapted to be positioned on an atrial side of the heart valve; and
   a connector directly connected to the inner end of the winding at the center of the first section, extending from the center of the first section, and connecting the first section to the second section.

2. A device as in claim 1, wherein the first section is substantially flat.

3. A device as in claim 1, wherein the first section is substantially conical.

4. A device as in claim 1, wherein the generally spiral shape of the first section is substantially circular.

5. A device as in claim 1, wherein the generally spiral shape of the first section is substantially elliptical.

6. A device as in claim 1, wherein the second section comprises a winding having a generally spiral shape, the winding of the second section emanating from a center of the second section and moving away from the center of the second section as it winds around the center of the second section.

7. A device as in claim 6, wherein the second section is substantially flat.

8. A device as in claim 6, wherein the second section is substantially conical.

9. A device as in claim 6, wherein the generally spiral shape of the second section is substantially circular.

10. A device as in claim 6, wherein the generally spiral shape of the second section is substantially elliptical.

11. A device as in claim 1, wherein the connector is connected to the center of the second section.

12. A device as in claim 11, wherein the connector is substantially straight.

13. A device as in claim 11, wherein the connector is curved.

14. A device as in claim 1, wherein the device, including the first section, comprises a wire, bundle of wires, strip, rod, tube or a combination thereof.

15. A device as in claim 14, wherein the wire, bundle of wires, strip, rod or tube has a circular cross-section.

16. A device as in claim 14, wherein the wire, bundle of wires, strip, rod or tube has an elliptical cross-section.

17. A device as in claim 14, wherein the wire, bundle of wires, strip, rod or tube has a rectangular, square or other non-round cross-section.

18. A device as in claim 14, wherein the wire, bundle of wires, strip, rod or tube has different cross-sections at different places along its length.

19. A device as in claim 14, wherein at least one end of the wire, bundle of wires, strip, rod or tube is rounded.

20. A device as in claim 14, wherein the wire, bundle of wires, strip, rod or tube has a groove in its outer surface.

21. A device as in claim 20, wherein the groove in the outer surface of the wire, bundle of wires, strip, rod or tube extends around the perimeter of the wire, bundle of wires, strip, rod or tube.

22. A device as in claim 20, wherein the groove in the outer surface of the wire, bundle of wires, strip, rod or tube extends in the direction of the length of the wire, bundle of wires, strip, rod or tube.

23. A device as in claim 20, wherein the groove in the outer surface of the wire, bundle of wires, strip, rod or tube extends in a substantially helical path along the wire, bundle of wires, strip, rod or tube.

24. A device as in claim 14, wherein the wire, bundle of wires, strip, rod or tube has one or more holes.

25. A device as in claim 14, further comprising a coating on the wire, bundle of wires, strip, rod or tube.

26. A device as in claim 25, wherein the coating is a drug-release coating.

27. A device as in claim 1, wherein the device is comprised at least in part of a metallic material.

28. A device as in claim 1, wherein the device is comprised at least in part of a shape memory metal material.

29. A device as in claim 1, wherein the device is comprised at least in part of nitinol.

30. A device as in claim 1, wherein the device is comprised at least in part of a plastic material.

31. A device as in claim 1, wherein the device is comprised at least in part of a composite material.

32. A device as in claim 1, wherein the device further comprises at least one anchoring element for anchoring the device to heart tissue.

33. A device as in claim 1, wherein the device further comprises a sensor.

34. A device as in claim 33, wherein the sensor is at least one of a pressure sensor, a temperature sensor, or a velocity sensor.

* * * * *